(12) United States Patent
Miyazaki

(10) Patent No.: US 7,420,368 B2
(45) Date of Patent: Sep. 2, 2008

(54) MAGNETIC RESONANCE IMAGING APPARATUS AND MAGNETIC RESONANCE IMAGING METHOD

(75) Inventor: Mitsue Miyazaki, Mount Prospect, IL (US)

(73) Assignees: Kaibushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 41 days.

(21) Appl. No.: 11/411,234

(22) Filed: Apr. 26, 2006

(65) Prior Publication Data

US 2007/0229070 A1 Oct. 4, 2007

(30) Foreign Application Priority Data

Apr. 4, 2006 (JP) ............................ P2006-103266

(51) Int. Cl.
*G01V 3/00* (2006.01)
(52) U.S. Cl. ...................................................... 324/307
(58) Field of Classification Search .......... 324/300–322
See application file for complete search history.

(56) References Cited

U.S. PATENT DOCUMENTS 5,510,713 A * 4/1996 Bernstein .................... 324/309
5,677,626 A * 10/1997 Miyazaki et al. ............ 324/307
5,757,188 A 5/1998 Miyazaki
6,900,632 B2 * 5/2005 Uetake ....................... 324/307

OTHER PUBLICATIONS

Miyazaki et al., "A Polarity Altered Spectral and Apatial Selective Acquisition Technique", Proceedings, ISMRM, 3rd Annual Meeting, Nice, p. 657, 1995.

* cited by examiner

*Primary Examiner*—Brij B Shrivastav
*Assistant Examiner*—Dixomara Vargas
(74) *Attorney, Agent, or Firm*—Nixon & Vanderhye PC

(57) ABSTRACT

A magnetic resonance imaging apparatus comprises: a chemical shift data storage unit, a first frequency adjusting unit, a first imaging unit, a second frequency adjust unit and a second imaging unit. The chemical shift data storage unit stores chemical shift data. The first frequency adjusting unit adjusts a center frequency of a first excitation pulse to a resonant frequency of a designated first substance. The first imaging unit generates an image in which the first substance is enhanced by performing a chemical shift imaging scanning with the first excitation pulse. The second frequency adjust unit automatically adjusts a center frequency of a second excitation pulse to a resonant frequency of a preliminarily designated second substance in accordance with chemical shift data. The second imaging unit generates an image in which the second substance is enhanced by performing a chemical shift imaging scanning with the second excitation pulse.

46 Claims, 15 Drawing Sheets

|  | Water | Saline | Fat | Silicone |
|---|---|---|---|---|
| (1)FSE+15_pasta | Visible | Visible | Suppressed | Suppressed |
| (2)FSE+15_pastaSi without FatSat | Suppressed | Suppressed | Visible | Visible |
| (3)FSE+15_pastaSi with FatSat | Suppressed | Suppressed | Suppressed | Visible |

MAGNETIC RESONANCE IMAGING APPARATUS AND MAGNETIC RESONANCE IMAGING METHOD

CROSS REFERENCES TO RELATED APPLICATIONS

The present application relates to and incorporates by reference Japanese Patent application No. 2006-103266 filed on Apr. 4, 2006.

BACKGROUND OF THE INVENTION

1. Field of the Invention

The present invention relates to a magnetic resonance imaging apparatus and a magnetic resonance imaging method which excite nuclear spin of an object magnetically with a RF (radio frequency) signal having the Larmor frequency and reconstruct an image based on a MR (magnetic resonance) signal generated due to the excitation, and more particularly, to a magnetic resonance imaging apparatus and a magnetic resonance imaging method which image substances showing mutually different chemical shifts selectively by adjusting a center frequency of an excitation pulse 2. Description of the Related Art Magnetic Resonance Imaging (MRI) is an imaging method which excite nuclear spin of an object set in a static magnetic field with a RF signal having the Larmor frequency magnetically and reconstruct an image based on a MR signal generated due to the excitation.

In the field of magnetic resonance imaging, chemical shift imaging for selectively imaging a specific substance is performed taking advantage of the variation in chemical shift from one substance constituting an object to another. The chemical shift is a variation in magnetic resonant frequency occurring due to the screening effect of orbital electrons. In view of examples of water and fat representative of the tissue of a living body, it is known that the resonant frequency of fat is shifted by about 3.5 ppm (parts per million) with respect to the resonant frequency of water (0 ppm in chemical shift).

This makes it possible to perform imaging by the fat suppression method for frequency-selectively suppressing signals from fat, or the water suppression method for frequency-selectively suppressing signals from water, by taking advantage of the difference in the center frequency for magnetic resonance. However, the peak of resonant frequency based on a chemical shift is influenced by the uniformity of a static magnetic field intensity, and if the uniformity of the static magnetic field intensity is imperfect, the peak of resonant frequency is also imperfect, thereby making it difficult to identify a substance. Hence, in the imaging by the fat suppression method or water suppression method taking advantage of chemical shift, shimming for adjusting the uniformity of the static magnetic field intensity is performed prior to the imaging in order to make clear the peak of resonant frequency in response to a substance.

Now, an attempt to selectively image not only fat but also silicone used as a material of a breast implant, by the chemical shift imaging, is under way. The materials used as a breast implant include saline in addition to silicone. In recent years, an influence of the leakage of silicone upon a normal mammary tissue is being turned into problem, and a saline implant having higher safety has been used more frequently. The interest of patients is, therefore, being focused on whether the material for an implant is silicone or saline.

However, an appropriate examination method for determining whether the implant is constituted of silicone or saline has not yet been established. As a result, a complicated examination method is now used wherein imaging such that the center frequency of excitation pulse is set to the resonant frequency of saline or water is performed to selectively image saline or water, and thereafter, imaging such that the center frequency of excitation pulse is set to the resonant frequency of silicone to selectively image silicone. In other words, the breast implant imaging requires a water image obtained by frequency-selectively enhancing signals from water, and a silicone image obtained by frequency-selectively enhancing signals from silicon.

FIG. 23 is a flowchart showing a conventional procedure of a chemical shift imaging of water and silicone, wherein symbols S each denote a step in the flowchart.

First, in step S1, first-time shimming is performed by an operation by an operator, and the uniformity of the static magnetic intensity is adjusted. Specifically, a current to be supplied to a shim coil provided for adjusting the static magnetic intensity is controlled.

Next, in step S2, a scan is performed for acquiring a frequency spectrum representing the resonant frequency of each substance based on a chemical shift. The frequency spectrum acquired by this scan allows the peak of the resonant frequency of water or saline to be detected.

Then, in step S3, the center frequency of excitation pulse for imaging is set to the resonant frequency of saline or water. The chemical shift of the resonant frequency of saline is 0.2 ppm, and hence, even if signals from water, of which the chemical shift in resonant frequency is 0 ppm, are selectively imaged, whether the implant is silicone or saline can be determined. Therefore, for example, the center frequency of excitation pulse is set to the resonant frequency of water.

Sometimes a series of work from the adjustment of the uniformity of static magnetic intensity up to the setting of the center frequency of excitation pulse is referred to as "shimming", but here, adjustment work of the uniformity of static magnetic intensity is designated as "shimming".

Next, in step S4, imaging is performed with the center frequency of excitation pulse set to the resonant frequency of water. This allows a water image obtained by frequency-selectively enhancing signals from water to be acquired.

Next, it is necessary to perform imaging in which the center frequency of excitation pulse is set to the resonant frequency of silicone. Here, the chemical shift of the resonant frequency of silicone is about −5 ppm with respect the resonant frequency of water (0 ppm in chemical shift). Accordingly, based on the frequency spectrum already acquired, the center frequency of excitation pulse can be set to the peak of the resonant frequency of silicone. However, some apparatus cannot change the center frequency of excitation pulse unless shimming and a scan for frequency spectrum acquisition are performed.

For such an apparatus, a second-time shimming is performed by an operation by the operator in step S5.

Then, in step S6, a scan for acquiring a frequency spectrum is performed. From the frequency spectrum obtained by this scan, a peak of the resonant frequency of silicone can be detected.

Next, in step S7, the center frequency of excitation pulse is set to the resonant frequency of silicone.

Then, in step S8, imaging is performed with the center frequency of excitation pulse set to the resonant frequency of silicone. This allows silicone image obtained by frequency-selectively enhancing signals from silicone to be acquired.

On the other hand, in order to improve the fat suppression effect utilizing chemical shift, a PASTA (polarity altered spectral-spatial selective acquisition) sequence has been devised for performing imaging by using in combination 90° RF pulse for proton excitation and 180° RF pulse for refocus, and making mutually opposite the polarities of first and second gradient magnetic fields for slice selection, the first and second gradient magnetic fields being applied along with the 90° RF pulse and 180° RF pulse, respectively (for example, refer to Japanese Patent Application (Laid-Open) No. 9-122101; or Miyazaki M, Takai H, Tokunaga Y, Hoshino T, and Hanawa M: A polarity altered spectral and spatial acquisition technique in "Proceedings, ISMRM, 3rd Annual Meeting" Nice, p. 657, 1995).

That is, the imaging by the PASTA sequence employs the first gradient magnetic field for slice selection, applied along with 90° RF pulse, and the second gradient magnetic field for slice selection, applied along with the 180° RF pulse. The second gradient magnetic field is made opposite in polarity to the first gradient magnetic field. Here, the frequency bandwidth of 90° RF pulse is set to a narrow width such as to prevent the resonant frequency band of water and that of fat from overlap each other there, that is, such as to be able to select water and fat utilizing chemical shifts. Conversely, the frequency bandwidth of the 180° RF pulse is set to a width such as to be able to refocus both of water and fat.

When, for example, fat suppression is performed using such a PASTA sequence, the protons in a water portion, excited by the 90° RF pulse are refocused by the 180° RF pulse under the gradient magnetic field having a polarity opposite to that in the excitation mode. As a result, echo signals occur from the protons in the water portion. On the other hand, the protons in a fat portion are refocused by the 180° RF pulse without being affected by the 90° RF pulse. Consequently, no echo signal occurs from the protons in the fat portion. This allows an achievement of a water image by fat suppression.

However, in the conventional chemical shift imaging, when attempting to selectively image each one of a plurality of different substances by using advantage of differences in chemical shift, it is necessary to preliminarily perform complicated work such as shimming, a scan for a frequency spectrum, an adjustment of the center frequency of excitation pulse by the operator, for each of the substances every imaging. For example, as described above, the operator must perform each of the shimming for selective acquisition and a scan for frequency spectrum acquisition regarding water signals, and shimming for selective acquisition and a scan for frequency spectrum acquisition regarding fat signals or silicone signals. In addition to the shimming, the operator must change the center frequency of excitation pulse each time the operator performs imaging about substances mutually different in chemical shift. For example, in the imaging of a breast implant, the operator must change the center frequency of excitation pulse from the resonant frequency of water into that of silicone.

Particularly when the operator without knowledge of chemical shift operates the apparatus, there is a possibility that proper shimming and/or the setting of the center frequency of excitation pulse may be difficult, with the result that an intended image may be unable to be obtained. Conversely, when the operator performs imaging utilizing chemical shift, there occurs a need for the operator to acquire knowledge thereof, which becomes a factor responsible for reduction in convenience of the magnetic resonance imaging apparatus. Furthermore, the imaging of molecules of drug or the like requires very detailed knowledge of chemical shift, and hence, under the current circumstances, substances that can be treated as targets of chemical shift imaging are limited to specific substances such as water, fat and the like.

Also, when shimming is not properly performed, or when a peak of frequency spectrum is detected by the operator without sufficient knowledge of chemical shift, an erroneous frequency is recognized as a resonant frequency, thereby causing a problem in that an improper frequency may be erroneously set as the center frequency of excitation pulse.

SUMMARY OF THE INVENTION

The present invention has been made in light of the conventional situations, and it is an object of the present invention to provide a magnetic resonance imaging apparatus and a magnetic resonance imaging method which make it possible to image properly by using chemical shifts of substances serving as targets with an easier operation.

The present invention provides a magnetic resonance imaging apparatus comprising: a chemical shift data storage unit configured to store chemical shift data of a plurality of substances which are to be targets for chemical shift imaging; a first frequency adjusting unit configured to adjust a center frequency of a first excitation pulse to a resonant frequency of a designated first substance; a first imaging unit configured to acquire a first magnetic resonant signal from a region containing the first substance by performing a first chemical shift imaging scanning with the first excitation pulse and generate an image in which the first substance is enhanced by using the first magnetic resonant signal; a second frequency adjust unit configured to automatically adjust a center frequency of a second excitation pulse to a resonant frequency of a preliminarily designated second substance in accordance with chemical shift data about at least one of the first substance and the second substance stored in the chemical shift data storage unit; and a second imaging unit configured to acquire a second magnetic resonant signal from a region containing the second substance by performing a second chemical shift imaging scanning with the second excitation pulse and generate an image in which the second substance is enhanced by using the second magnetic resonant signal, in an aspect to achieve the object.

The present invention also provides a magnetic resonance imaging apparatus comprising: a chemical shift data storage unit configured to store chemical shift data of a plurality of substances which are to be targets for chemical shift imaging; a first frequency adjusting unit configured to adjust a center frequency of a first excitation pulse to a resonant frequency of a first substance, the first substance being designated one of silicone and water; a first imaging unit configured to acquire a first magnetic resonant signal from a region containing the first substance by performing a first chemical shift imaging scanning with the first excitation pulse and generate an image in which the first substance is enhanced by using the first magnetic resonant signal; a second frequency adjust unit configured to automatically adjust a center frequency of a second excitation pulse to a resonant frequency of a second substance which is other of the silicone and the water in accordance with chemical shift data about the other stored in the chemical shift data storage unit; and a second imaging unit configured to acquire a second magnetic resonant signal from a region containing the second substance by performing a second chemical shift imaging scanning with the second excitation pulse and generate an image in which the second substance is enhanced by using the second magnetic resonant signal, in an aspect to achieve the object.

The present invention also provides a magnetic resonance imaging apparatus comprising: a substance designating unit configured to designate a substance which is to be a target for chemical shift imaging; a chemical shift data storage unit configured to store chemical shift data of substances which can be designated to the target; a frequency spectrum acquiring unit configured to acquire a frequency spectrum; a frequency adjusting unit configured to adjust a center frequency of an excitation pulse to a resonant frequency of silicone in accordance with chemical shift data of the silicone stored in the chemical shift data storage unit and the frequency spectrum in case where the silicone is designated by the substance designating unit; and an imaging unit configured to acquire a magnetic resonant signal from a region containing the silicone by performing chemical shift imaging scanning with the excitation pulse and generate an image in which the silicone is enhanced by using the magnetic resonant signal, in an aspect to achieve the object.

The present invention also provides a magnetic resonance imaging apparatus comprising: a substance designating unit configured to designate a substance which is to be a target for chemical shift imaging; a chemical shift data storage unit configured to store chemical shift data of substances which can be designated to the target; a frequency spectrum acquiring unit configured to acquire a frequency spectrum; a frequency adjusting unit configured to adjust a center frequency of an excitation pulse to a resonant frequency of the designated substance in accordance with chemical shift data about the designated substance stored in the chemical shift data storage unit and the frequency spectrum; and an imaging unit configured to perform chemical shift imaging scanning using a sequence of which a magnetizing condition is adjusted so as to enhance a magnetic resonance signal from the designated substance in accordance with chemical shift data about the designated substance and generate an image in which the designated substance is enhanced using the magnetic resonance signal acquired from a region containing the designated substance, in an aspect to achieve the object.

The present invention also provides a magnetic resonance imaging apparatus comprising: a chemical shift data storage unit configured to store chemical shift data of at least one of a first substance and a second substance; a frequency spectrum acquiring unit configured to acquire a frequency spectrum; and a resonant frequency correcting unit configured to correct a resonant frequency of the second substance to a resonant frequency of the first substance in accordance with the chemical shift data in either of a case where the resonant frequency of the second substance is erroneously acquired as the resonant frequency of the first substance in accordance with the frequency spectrum and a case where the resonant frequency of the second substance is acquired to obtain the resonant frequency of the first substance in accordance with the frequency spectrum, in an aspect to achieve the object.

The present invention also provides a magnetic resonance imaging method comprising steps of: adjusting a center frequency of a first excitation pulse to a resonant frequency of a designated first substance; acquiring a first magnetic resonant signal from a region containing the first substance by performing a first chemical shift imaging scanning with the first excitation pulse and generating an image in which the first substance is enhanced by using the first magnetic resonant signal; automatically adjusting a center frequency of a second excitation pulse to a resonant frequency of a preliminarily designated second substance in accordance with chemical shift data about at least one of the first substance and the second substance; and acquiring a second magnetic resonant signal from a region containing the second substance by performing a second chemical shift imaging scanning with the second excitation pulse and generating an image in which the second substance is enhanced by using the second magnetic resonant signal, in an aspect to achieve the object.

The present invention also provides a magnetic resonance imaging method comprising steps of: adjusting a center frequency of a first excitation pulse to a resonant frequency of a first substance, the first substance being designated one of silicone and water; acquiring a first magnetic resonant signal from a region containing the first substance by performing a first chemical shift imaging scanning with the first excitation pulse and generating an image in which the first substance is enhanced by using the first magnetic resonant signal; automatically adjusting a center frequency of a second excitation pulse to a resonant frequency of a second substance which is other of the silicone and the water in accordance with chemical shift data about the other; and acquiring a second magnetic resonant signal from a region containing the second substance by performing a second chemical shift imaging scanning with the second excitation pulse and generating an image in which the second substance is enhanced by using the second magnetic resonant signal, in an aspect to achieve the object.

The present invention also provides a magnetic resonance imaging method comprising steps of: designating a substance which is to be a target for chemical shift imaging; acquiring a frequency spectrum; adjusting a center frequency of an excitation pulse to a resonant frequency of silicone in accordance with chemical shift data of the silicone and the frequency spectrum in case where the silicone is designated as the substance which is to be the target; and acquiring a resonant signal from a region containing the silicone by performing chemical shift imaging scanning with the excitation pulse and generating an image in which the silicone is enhanced by using the magnetic resonant signal, in an aspect to achieve the object.

The present invention also provides a magnetic resonance imaging method comprising steps of: designating a substance which is to be a target for chemical shift imaging; acquiring a frequency spectrum; adjusting a center frequency of an excitation pulse to a resonant frequency of the designated substance in accordance with chemical shift data about the designated substance and the frequency spectrum; and performing chemical shift imaging scanning using a sequence of which a magnetizing condition is adjusted so as to enhance a magnetic resonance signal from the designated substance in accordance with chemical shift data about the designated substance and generating an image in which the designated substance is enhanced using the magnetic resonance signal acquired from a region containing the designated substance, in an aspect to achieve the object.

The present invention also provides a magnetic resonance imaging method comprising steps of: acquiring a frequency spectrum; and correcting a resonant frequency of a second substance to a resonant frequency of a first substance in accordance with chemical shift data of at least one of the first substance and the second substance in either of a case where the resonant frequency of the second substance is erroneously acquired as the resonant frequency of the first substance in accordance with the frequency spectrum and a case where the resonant frequency of the second substance is acquired to obtain the resonant frequency of the first substance in accordance with the frequency spectrum, in an aspect to achieve the object.

The magnetic resonance imaging apparatus and the magnetic resonance imaging method as described above make it possible to image properly by using chemical shifts of substances serving as targets with an easier operation.

DESCRIPTION OF THE PREFERRED EMBODIMENTS

A magnetic resonance imaging apparatus and a magnetic resonance imaging method according to embodiments of the present invention will be described with reference to the accompanying drawings.

Figure 1:
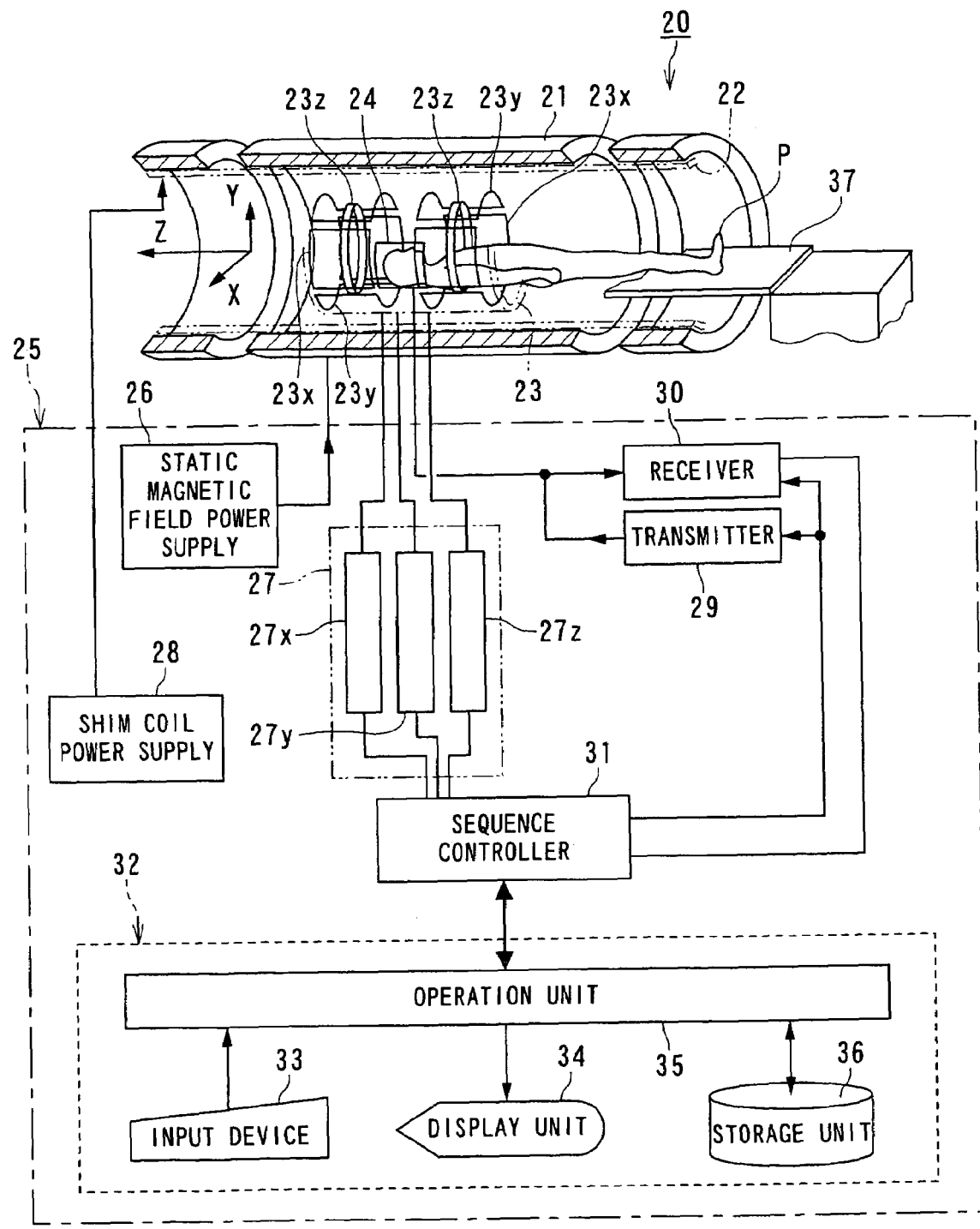
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil unit 23 and a RF coil 24. The static field magnet 21, the shim coil 22, the gradient coil unit 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a monitor 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil unit 23 includes an X-axis gradient coil unit 23x, a Y-axis gradient coil unit 23y and a Z-axis gradient coil unit 23z. Each of the X-axis gradient coil unit 23x, the Y-axis gradient coil unit 23y and the Z-axis gradient coil unit 23z which is cylinder-shaped is arranged inside the static field magnet 21. The gradient coil unit 23 has also a bed 37 in the area formed inside it which is an imaging area. The bed 37 supports an object P. Around the bed 37 or the object P, the RF coil 24 may be arranged instead of being built in the gantry.

The gradient coil unit 23 communicates with the gradient power supply 27. The X-axis gradient coil unit 23x, the Y-axis gradient coil unit 23y and the Z-axis gradient coil unit 23z of the gradient coil unit 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil unit 23x, the Y-axis gradient coil unit 23y and the Z-axis gradient coil unit 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a RF signal given from the transmitter 29 to the object P and receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex number data obtained through the detection of a MR signal and A/D conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

The computer 32 gets various functions by the operation unit 35 executing some programs stored in the storage unit 36 of the computer 32. The computer 32 may include some specific circuits instead of using some of the programs.

Figure 2:
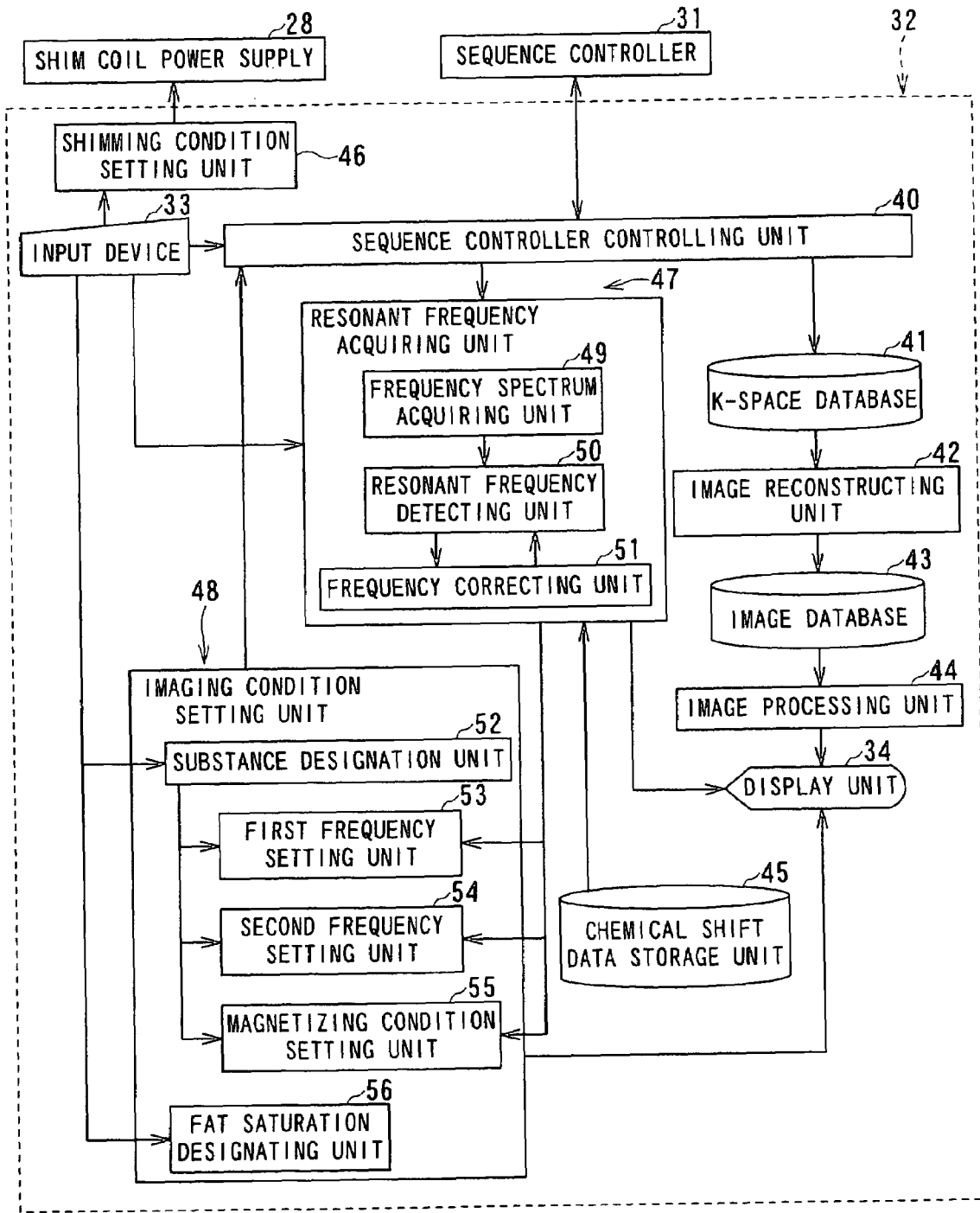
FIG. 2 is a functional block diagram of the computer in the magnetic resonance imaging apparatus shown in FIG. 1.

FIG. 2 is a functional block diagram of the computer 32 in the magnetic resonance imaging apparatus 20 shown in FIG. 1.

The computer 32 functions as a sequence controller control unit 40, a k-space database 41, an image reconstructing unit 42, an image database 43, an image processing unit 44, a chemical shift data storage unit 45, a shimming condition setting unit 46, a resonant frequency acquiring unit 47 and an imaging condition setting unit 48 by reading the programs The sequence controller controlling unit 40 includes a function of causing the sequence controller 31 to drive based on information from the input device 33 or another element, by providing the sequence controller 31 with a required pulse sequence received from the imaging condition setting unit 48, and a function of receiving raw data serving as k-space data from the sequence controller 31 and disposing the k-space data in a k-space (Fourier space) formed in the k-space database 41. Here, the sequence controller controlling unit 40 is configured to acquire parameters necessary for the execution of a pulse sequence from the input device 33 or the other element and provide them to the sequence controller 31.

Thereby, in the k-space database 41, each of the pieces of raw data generated in the receiver 30 is stored as k-space data, which is disposed in the k-space formed in the k-space database 41.

The image reconstructing unit 41 has a function for capturing the k-space data from the k-space database 41, performing predetermined image reconstruction processing, such as three dimensional (3D) Fourier transform processing, reconstructing three dimensional image data of the object P, and writing the image data to the image data database 43. Incidentally, intermediate data, such as two dimensional (2D) image data, may be temporarily generated by processing, such as two dimensional Fourier transform processing, and thereafter the three dimensional image data may be reconstructed.

Therefore, the image data database 43 stores the three dimensional image data of the object P.

The image processing unit 44 has a function of performing necessary image processing to a three-dimensional image data read from the image database 43, and causing the display unit 34 to display the processing result.

The chemical shift data storage unit 45 stores, as chemical shift data, values of resonant frequencies inherent in substances that have been chemically shifted, and relative shift values of resonant frequencies of substances with respect to the resonant frequency of a specific substance such as water.

Figure 3:
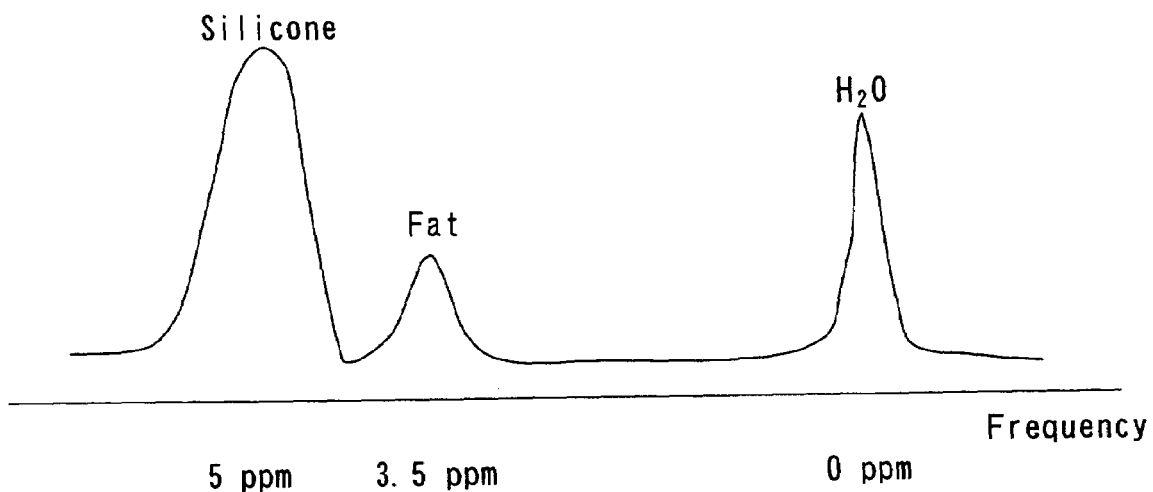
FIG. 3 is a diagram showing an example of a frequency spectrum upon which chemical shift data stored in the chemical shift data storage unit shown in FIG. 2 is based.

FIG. 3 is a diagram showing an example of a frequency spectrum upon which chemical shift data stored in the chemical shift data storage unit 45 shown in FIG. 2 is based.

In FIG. 3, the abscissa denotes a frequency, and the ordinate denotes signal intensity. As shown in FIG. 3, signal intensities of silicone, fat, and water exhibit peaks at their respective resonant frequencies. Specifically, due to chemical shift, the resonant frequency of fat is shifted by 3.5 ppm, and the resonant frequency of silicone is shifted by 5 ppm each with respect to the resonant frequency of water constituting the reference (i.e., 0 ppm in chemical shift). Besides the resonant frequencies of silicone, fat, water shown in FIG. 3, those of saline and various substances used for drugs and the like can be individually stored into the chemical shift data storage unit 45, as chemical shift data.

While the frequency spectrum as shown in FIG. 3 can be obtained by a scan for frequency spectrum acquisition, it varies from one imaging area to another, and from one object to another. Simultaneously, the frequency spectrum varies depending on various conditions such as static magnetic field distribution, and so on. Also, if the uniformity of a static magnetic field formed by the static field magnet 21 is low, there occurs a possibility that a satisfactory peak of resonant frequency will be unable to be obtained in a frequency spectrum under the influence of nonuniformity of the static magnet field. Such being the case, in the chemical shift imaging, shimming for adjusting the uniformity of static magnetic field is performed each time an imaging area or object varies, and thereafter, a frequency spectrum is acquired by a scan. Then, based on the acquired frequency spectrum, the chemical shift data stored in the chemical shift data storage unit 45 is corrected. Out of the correction, the correction for shifting chemical shift data by a constant value is particularly referred to as a "zero-order correction".

The shimming condition setting unit 46 has a function of adjusting a current supplied from the shim coil power supply 28 to the shim coil 22 by providing the shim coil power supply 28 with a control signal in accordance with instruction information received from the input device 33. This allows shimming for uniformalizing the static magnetic field to be executed.

The resonant frequency acquiring unit 47 has a function of determining the resonant frequency of a substance to be imaged by chemical shift imaging, i.e., a frequency to be set to the center frequency of excitation pulse. To this end, the resonant frequency acquiring unit 47 includes the frequency spectrum acquiring unit 49, resonant frequency detecting unit 50, and frequency correcting unit 51.

The frequency spectrum acquiring unit 49 has a function of acquiring a frequency spectrum by receiving data acquired by a scan for frequency spectrum acquisition from the sequence controller controlling unit 40, and a function of providing the acquired frequency spectrum to the resonant frequency detecting unit 50. Also, the frequency spectrum acquiring unit 49 is configured to display the frequency spectrum on the display unit 34 based on instruction information received from the input device 33.

The resonant frequency detecting unit 50 has a function of detecting the resonant frequency of at least one substance out of a frequency spectrum received from the frequency spectrum acquiring unit 49, and providing the detected resonant frequency to the frequency correcting unit 51 together with identification information about the at least one substance. The detecting methods for a resonant frequency include a method for detecting the maximum value of a frequency spectrum and a method for detecting the peak of the frequency spectrum. When detecting the peak of the frequency spectrum, there is a possibility that a plurality of peaks will be detected. Then, the plurality of resonant frequencies of substances may also be detected.

The detecting method for a resonant frequency can be determined by indicating by the input device 33. The detection result can be displayed on the display unit 34. The resonant frequency detecting unit 50 is configured so that, when instructed to automatically detect a substance corresponding to a resonant frequency by the input device 33, it can make reference to chemical shift data stored in the chemical shift data storage unit 45 to automatically detect a substance corresponding to the resonant frequency.

The frequency correcting unit 51 includes a function of correcting chemical shift data acquired from the chemical shift data storage unit 45, by using the resonant frequency of at least one substance, received from the resonant frequency detecting unit 50, and a function of providing the corrected chemical shift data to the imaging condition setting unit 48. That is, the frequency correcting unit 51 has a function of determining a difference between the resonant frequency of a certain substance, acquired by a scan and the resonant frequency of the corresponding substance, acquired from the chemical shift data storage unit 45, and performing a zero-order correction by shifting the overall chemical shift data by the determined difference value. Also, the frequency correcting unit 51 is configured to correct the coefficients of a first or higher order of chemical shift data that has been converted into a mathematical expression, based on a frequency spectrum acquired in the frequency spectrum acquiring unit 49.

Moreover, the frequency correcting unit 51 has a function of making a correction to the correct resonant frequency based on the chemical shift data stored in the chemical shift data storage unit 45, when the resonant frequency of a substance other than an intended substance is erroneously recognized as the resonant frequency of the intended substance by the resonant frequency detecting unit 50. Particularly, it is practical to provide the frequency correcting unit 51 with a function of correcting the resonant frequency of water based on the difference between the resonant frequencies of silicone and water, stored in the chemical shift data storage unit 45 when the resonant frequency of silicone is erroneously recognized as that of water.

Figure 4:
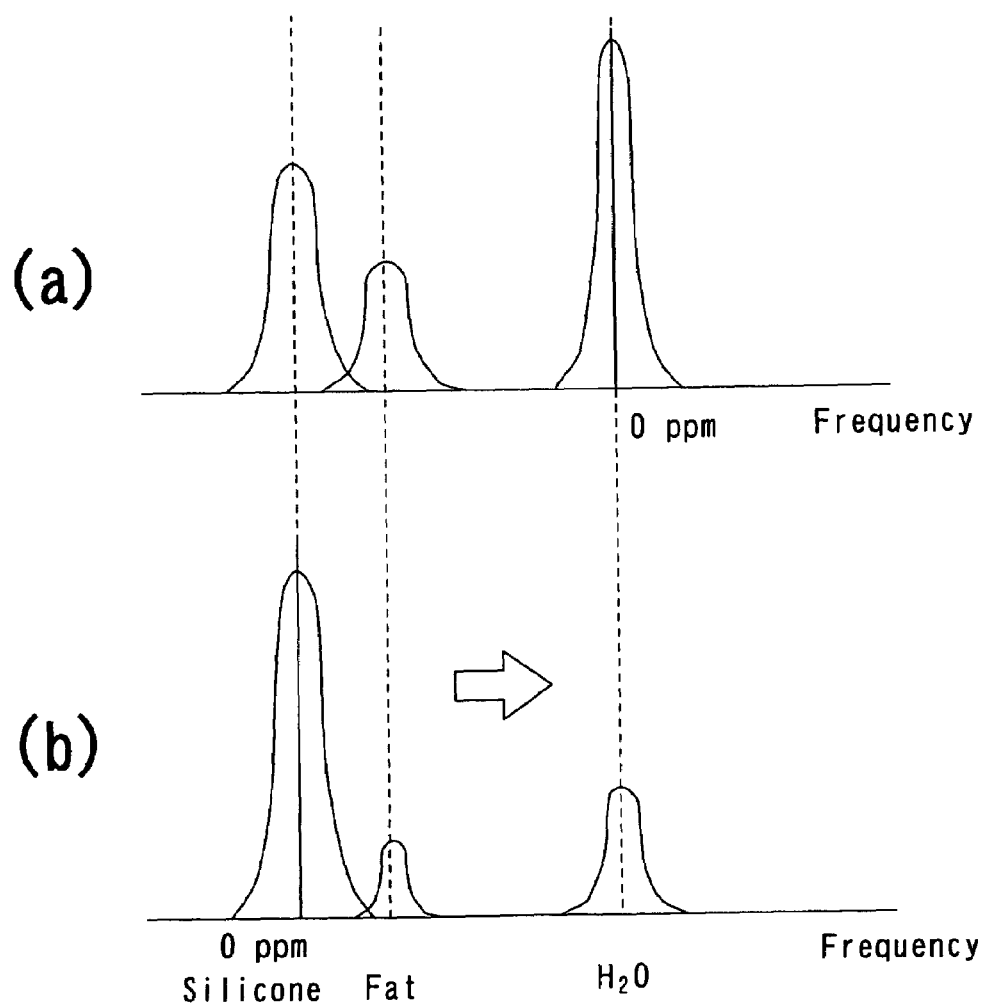
FIG. 4 is a diagram showing an example in which the resonant frequency of silicone is erroneously recognized as that of water in the resonant frequency detecting unit.

FIG. 4 is a diagram showing an example in which the resonant frequency of silicone is erroneously recognized as that of water in the resonant frequency detecting unit 50.

In FIG. 4(a) and 4(b), the abscissa denotes a frequency, and the ordinate denotes a signal intensity. FIG. 4(a) shows an example of frequency spectrum obtained by data from the mammary tissue of an object, and FIG. 4(b) shows an example of frequency spectrum obtained by data from the mammary tissue of another object.

As shown in FIG. 4(a) and 4(b), the signal intensity from each substance varies depending on the object or imaging area. Specifically, as shown in FIG. 4(a), the maximum value in a frequency spectrum usually becomes the center frequency of the resonant frequency band of water. However, some objects are different in components of the mammary tissue, and as shown in FIG. 4(b), the resonant frequency of silicone may become the maximum value in a frequency spectrum.

For example, when attempting to determine the resonant frequency of water, if a maximum value is detected from the frequency spectrum in which the signal intensity exhibits the maximum at the resonant frequency of water as shown in FIG. 4(a), the resonant frequency of water can be determined as being 0 ppm in chemical shift. However, as shown in FIG. 4(b), if a maximum value is detected from the frequency spectrum in which the signal intensity exhibits the maximum at the resonant frequency of silicone, based on the presumption that the frequency spectrum take the maximum value at the resonant frequency of water, then, the resonant frequency of silicone is detected as that of water with the chemical shift being 0 ppm. In other words, the resonant frequency of silicone is undesirably misrecognized as that of water. This misrecognized frequency, therefore, must be set to the correct resonant frequency of water.

Such misrecognition can occur, for example, when, after having caused a plurality of peaks detected from the frequency spectrum to be displayed on the display unit 34, the operator selects a single peak by an operation of the input device 33, or when the maximum value in the frequency spectrum is detected.

On the other hand, if a peak on the lowest frequency side is detected from the frequency spectrum, it is possible to reliably obtain the resonant frequency of water irrespective of the magnitude of the signal intensity from each of the substances. That is, if a peak on the most right-hand side is detected in FIG. 4(a) and 4(b), the resonant frequency of water can be reliably determined irrespective of whether from the frequency spectrum as shown in FIG. 4(a), or from the frequency spectrum as shown in FIG. 4(b).

Accordingly, the frequency correcting unit 51 has a function of detecting whether the resonant frequency has been erroneously recognized, when there is a possibility that the resonant frequency may have been erroneously recognized as in the case where a specific resonant frequency is determined, accompanied with an operation of the input device 33 by the operator, or the case where a specific resonant frequency is determined by detecting the maximum value in the frequency spectrum; and has a function of making a correction to the correct resonant frequency when it is detected that the resonant frequency has been erroneously recognized as that of another substance. The detection whether the resonant frequency has been erroneously recognized, is possible, for example, by the frequency correcting unit 51 instructing the resonant frequency detecting unit 50 to detect the peak of the position corresponding to a pertinent substance (for example, when the resonant frequency of water is determined, the peak on the lower frequency side) from the frequency spectrum, and by comparing a resonant frequency, as the result of the instruction, acquired again from the resonant frequency detecting unit 50 and a resonant frequency having a possibility of being erroneously recognized. Specifically, if the resonant frequency obtained by detecting the peak of the position corresponding to the substance from the frequency spectrum can be identified with the resonant frequency having a possibility of having been erroneously recognized, then, it can be determined that the resonant frequency has not been erroneously recognized.

However, the determination whether the resonant frequency is erroneously recognized, can be performed by an arbitrary method. For example, when the threshold value to a shift amount of chemical shift data by the zero-order correction is set in advance and the shift amount exceeds the set threshold value, it may be determined that the resonant frequency is erroneously recognized, accompanied with an confirmation display to the operator. Alternatively, the operator may determine the presence/absence of erroneous recognition by causing the display unit 34 to display a resonant frequency having a possibility of having been erroneously recognized. Still alternatively, the arrangement may be such that, when it is determined that the resonant frequency has been erroneously recognized, the resonant frequency may be manually corrected by an operation of the input device 33.

In particular, silicone is provided inside an object P in a state of being enclosed in a bag at a constant concentration, so that its signal intensity is often higher than that of a water signal or a fat signal. As a result, the detection of the resonant frequency of silicone is comparatively easy. Therefore, not only when the resonant frequency is erroneously recognized, but also when the intensity of a water signal or a fat signal is so low that the detection of the resonant frequency of water or fat is difficult, it is possible to intentionally detect the resonant frequency of silicone in order to determine the resonant frequency of water or fat, and thereby determine the resonant frequency of water or fat from the detected resonant frequency of the silicone, based on the chemical shift value. This function of determining the resonant frequency of water or fat by detecting the silicone signals is also provided in the frequency correcting unit 51, and can be modally operated in a resonant frequency detecting mode.

That is, the association between the resonant frequency detected in the resonant frequency detecting unit 50 and a substance, the determination as to whether the resonant frequency has been erroneously recognized, and the correction of the resonant frequency when the resonant frequency has been erroneously determined as the resonant frequency of another substance, can be automatically performed in the resonant frequency acquiring unit 47, and can also be manually performed, with an operation of the input device 33 by the operator. The changeover as to whether to automatically perform or manually perform the above-described items, i.e., the association between the resonant frequency detected in the resonant frequency detecting unit 50 and a substance, the determination as to whether the resonant frequency has been erroneously recognized, and the correction of the resonant frequency when the resonant frequency has been erroneously determined as the resonant frequency of another substance, can be modally performed by the selection between an automatic mode and manual mode.

The imaging condition setting unit 48 includes a function of setting the pulse sequence, as an imaging condition for chemical shift imaging, and a function of providing the set pulse sequence to the sequence controller controlling unit 40. Here, the pulse sequence is not limited as long as it can be used for chemical shift imaging. Hence, the pulse sequences to be used may include a spin echo (SE) sequence, fast spin echo (FSE) sequence, fast advanced spin echo (FASE) sequence, echo planar imaging (EPI) sequence, etc. each involving the application of an excitation pulse and a refocus pulse.

In addition, a PASTA sequence, which has been devised to improve the fat suppressing effect utilizing chemical shift, a sequence using binomial pulses used for water excitation, as excitation pulses, and a sequence in conformance with the three-point Dixon method can also be employed for chemical shift imaging.

Performing chemical shift imaging by adjusting magnetizing conditions of the above-described sequences makes it possible to perform molecular imaging for frequency-selectively exciting an arbitrary substance of which the chemical shift value is known, such as not only water and fat but also silicone, saline, a drug, etc., to thereby acquire echo signals, and for imaging the acquired echo signals. In particular, by using the PASTA sequence, the sequence using binomial pulses, or the three-point Dixon sequence, as a sequence for chemical shift imaging, it can be expected that signals from a specific substance are separated from signals from a substance to be suppressed, in a more reliable manner.

So, the description herein will be made of a setting method for imaging conditions when the PASTA sequence, the sequence using the binomial pulses, and the three-point Dixon sequence are each used as a sequence for chemical shift imaging.

Figure 5:
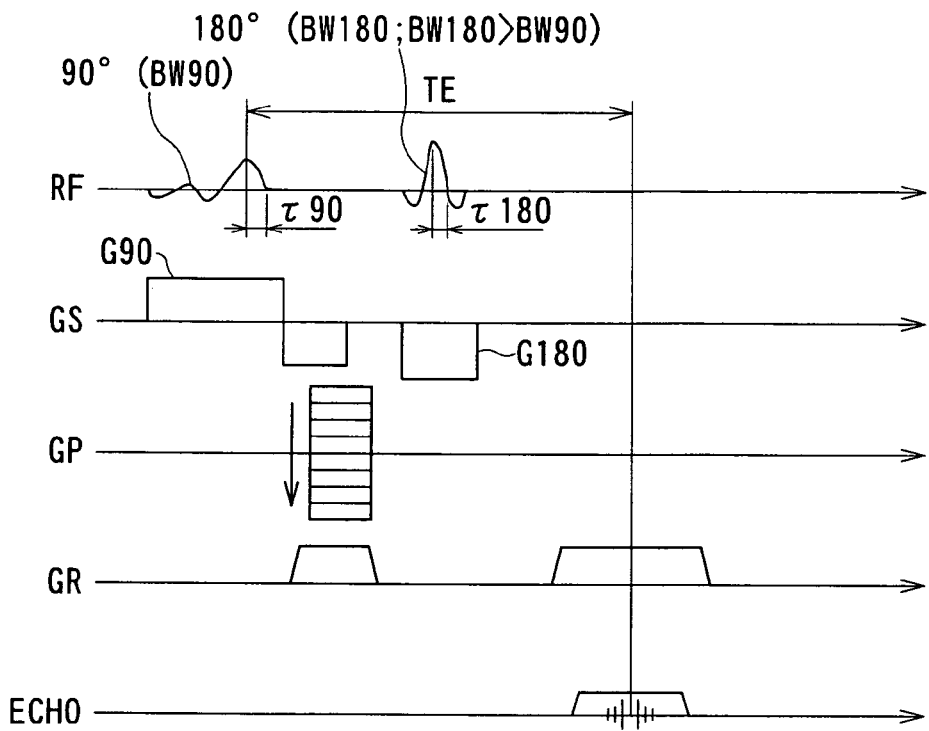
FIG. 5 is a schematic view of the PASTA sequence set in the imaging condition setting unit shown in FIG. 2.

FIG. 5 is a schematic view of the PASTA sequence set in the imaging condition setting unit 48 shown in FIG. 2.

In FIG. 5, a reference character RF denotes an RF signal to be transmitted to an imaging area. Reference characters GS, GP, GR, and ECHO, respectively, denote a gradient magnetic field for slice selection, a gradient magnetic field for phase encode, a gradient magnetic field for readout, and an echo signal.

As shown in FIG. 5, in the PASTA sequence, a 90° excitation pulse, of which the frequency bandwidth is BW90 and the τ length (lobe length) is τ90, is applied. Subsequently, a 180° refocus pulse, of which the frequency bandwidth is BW180 and the τ length is τ180, is applied. Also, the gradient magnetic field GS for slice selection, the gradient magnetic field GP for phase encode, and the gradient magnetic field GR for readout are each applied. Thereupon, at an echo time (TE) after the application of the 90° excitation pulse, echo data is acquired.

The frequency bandwidth BW90 of the 90° excitation pulse is set to be narrower than the frequency bandwidth BW180 of the 180° refocus pulse. The gradient magnetic field G90 for slice selection, applied along with the 90° excitation pulse, and the gradient magnetic field G180 for slice selection, applied along with the refocus pulse, are made mutually opposite in polarity. FIG. 5 shows an example in which the polarity of the gradient magnetic field G90 for slice selection, applied along with the 90° excitation pulse is taken as positive, while the polarity the gradient magnetic field G180 for slice selection, applied along with the refocus pulse is taken as negative.

By controlling so that magnetizing conditions such as the frequency bandwidths BW90 and BW180, τ lengths τ90 and τ180 of the 90° excitation pulse and the 180° refocus pulse, and the gradient magnetic fields G90 and G180 for slice selection, which are respectively applied along with the 90° excitation pulse and the 180° refocus pulse, satisfy required conditions, it is possible to perform the molecular imaging utilizing chemical shift for generating echo signals from a specific substance to image them.

Figure 6:
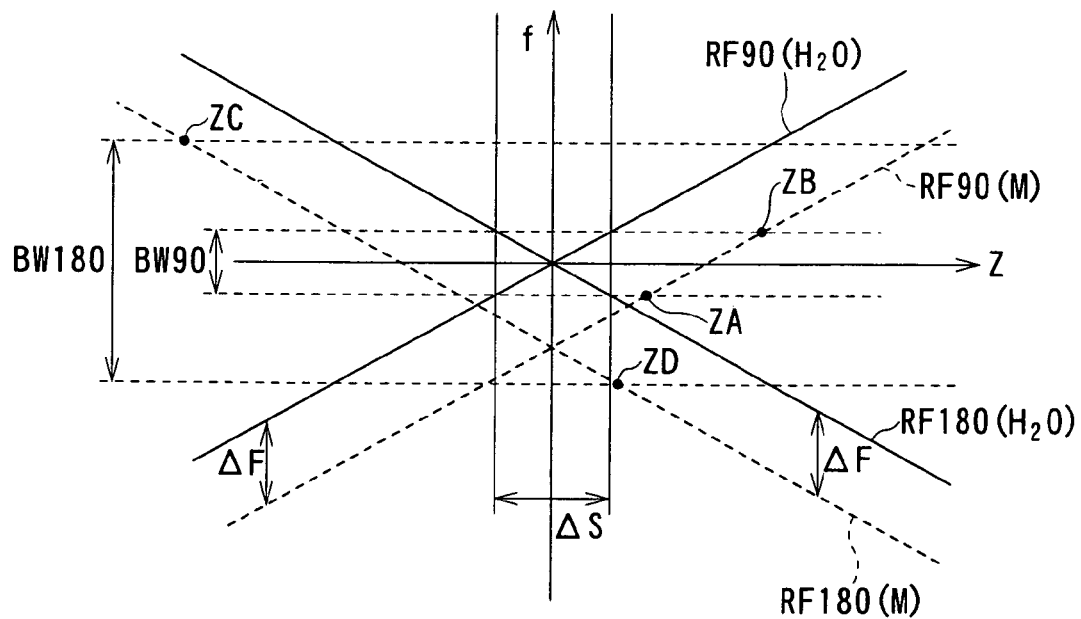
FIG. 6 is a diagram showing frequency areas that are excited and refocused by the execution of a scan by the PASTA sequence shown in FIG. 5.

FIG. 6 is a diagram showing frequency areas that are excited and refocused by the execution of a scan by the PASTA sequence shown in FIG. 5.

In FIG. 6, the abscissa denotes a position Z in the slice direction, and the ordinate denotes a frequency f. Here, RF90 (H2O) indicated by a solid line denotes the resonant frequency of water at a position Z in the slice direction in a state where the gradient magnetic field G90 for slice selection has been applied along with the 90° excitation pulse. On the other hand, RF180 (H2O) indicated by a solid line denotes the resonant frequency of water at a position Z in the slice direction in a state where the gradient magnetic field G180 for slice selection has been applied along with the 180° refocus pulse. Since the polarity of the gradient magnetic field G90 for slice selection, applied along with the 90° excitation pulse, and the polarity the gradient magnetic field G180 for slice selection, applied along with the 180° refocus pulse are opposite to each other, the positional change of the resonant frequency RF90 (H2O) of water in a state where the gradient magnetic field G90 for slice selection has been applied and the positional change of the resonant frequency RF180 (H2O) of water in a state where the gradient magnetic field G180 for slice selection has been applied, is axisymmetric with each other.

Here, letting the chemical shift value of a substance (M) having known chemical shift value, with respect to water be $\Delta F$, the positional change on the resonant frequency in the slice direction, of the substance (M) with the applied gradient magnetic field G90 for slice selection, becomes a straight line obtained by shifting the resonant frequency RF90 (H2O) of water along the frequency f direction by the chemical shift value $\Delta F$, like RF90 (M) indicated by a dotted line. Likewise, the positional change on the resonant frequency in the slice direction, of the substance (M) with the applied gradient magnetic field G180 for slice selection, becomes a straight line obtained by shifting the resonant frequency RF180 (H2O) of water along the frequency f direction by the chemical shift value $\Delta F$, like RF180 (M) indicated by a dotted line.

For example, when attempting to acquire echo signals from water in a slice with a slice thickness $\Delta S$ by the 90° excitation pulse while suppressing echo signals from a substance (M), it is advisable to set a frequency bandwidth BW90 of the 90° excitation pulse so as to overlap the resonant frequency RF90 (H2O) of water, and simultaneously so as not to overlap the resonant frequency RF90 (M) of the substance (M), at a position Z within the slice with a slice thickness $\Delta S$. On the other hand, when attempting to refocus proton spins contained in both of the substance (M) and water by the 180° refocus pulse, it is advisable to set a frequency bandwidth BW180 of the 180° refocus pulse so as to overlap both of the resonant frequency RF180 (H2O) of water and the resonant frequency RF180 (M) of the substance (M).

Herein, the condition for exciting protons in the water region without exciting protons in a region containing the substance (M), and refocusing the protons in both of the region containing the substance (M) and the water region, can be represented by the following expressing (1).

$$R = (\Delta S - |\Delta F / G90 - \Delta F / G180|) / \Delta S < 0 \qquad (1)$$

Note that, in the expression (1), R is an overlap ratio between a region (ZA-ZB) containing the substance (M) in the slice direction, excited by the 90° excitation pulse, and a region (ZC-ZD) containing the substance (M) in the slice direction, refocused by the 180° refocus pulse. Setting magnetizing conditions so that the overlap ratio R takes a negative value allows signals from the substance (M) to be completely suppressed.

Here, when using the following expressions (2-1) and (2-2) that show the respective relationships between the $\tau$ lengths $\tau$90 and $\tau$180 of the 90° excitation pulse and the 180° refocus pulse, and the gradient magnetic fields G90 and G180 for slice selection, the above-described expression (1) can be represented as the following expression (2-3).

$$|G90| = \tau 90 / \Delta S \qquad (2\text{-}1)$$

$$|G180| = \tau 180 / \Delta S \qquad (2\text{-}2)$$

$$R = 1 - |\Delta F \cdot (\tau 90 + \tau 180)| < 0 \qquad (2\text{-}3)$$

Therefore, the conditions for acquiring signals from water while suppressing signals from the substance (M) are represented by the following expressions (3-1) and (3-2), and in addition, the expression (3-3) derived from the expression (2-3).

$$BW90 < BW180 (\tau 180 > \tau 90) \qquad (3\text{-}1)$$

$$|G90| = -|G180| \qquad (3\text{-}2)$$

$$\tau 90 + \tau 180 > 1 / \Delta F \qquad (3\text{-}3)$$

Hence, setting imaging conditions such as to satisfy the equations (3-1), (3-2) and (3-3) allows molecular imaging for acquiring an image with a specified substance enhanced to be performed. For example, when a chemical shift value of a particular drug to be a target of molecular imaging with respect to water is ±200 Hz, the following expression (4-2) becomes the condition for the respective $\tau$ lengths $\tau$90 and $\tau$180 of the 90° excitation pulse and the 180° refocus pulse, based on the following expression (4-1).

$$\Delta F = \pm 200 \text{ (Hz)} \qquad (4\text{-}1)$$

$$\tau 90 + \tau 180 > 5.00 \text{ (ms)} \qquad (4\text{-}2)$$

When attempting to obtaining an image by acquiring signals from water while suppressing signals from fat, the following expression (5-2) become the condition for the respective $\tau$ lengths $\tau$90 and $\tau$180 of the 90° excitation pulse and the 180° refocus pulse, based on the following expression (5-1), wherein a chemical shift value 230 Hz of fat with respect to water is used.

$$\Delta F = 230 \text{ (Hz)} \qquad (5\text{-}1)$$

$$\tau 90 + \tau 180 > 4.35 \text{ (ms)} \qquad (5\text{-}2)$$

In this manner, if a chemical shift value $\Delta F$ of a specified substance with respect to a substance constituting the reference such as water or fat, is known, molecular imaging for imaging the specified substance can be performed by setting magnetizing conditions from the chemical shift value $\Delta F$ of the specified substance as shown in the expressions (3-1) (3-2), and (3-3), and simultaneously setting the center frequency of the 90° excitation pulse to the resonant frequency of the specified substance.

Figure 7:
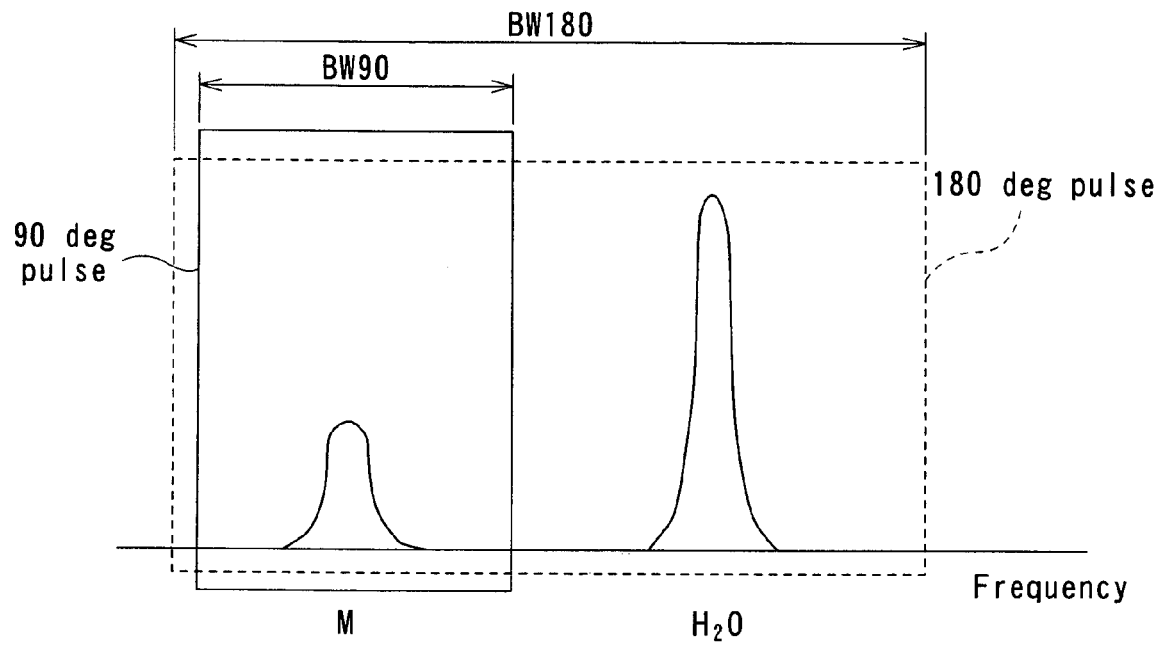
FIG. 7 shows a setting example of imaging condition in the imaging condition setting unit shown in FIG. 2 when molecular imaging is performed using the PASTA sequence.

FIG. 7 shows a setting example of imaging condition in the imaging condition setting unit 48 shown in FIG. 2 when molecular imaging is performed using the PASTA sequence.

In FIG. 7, the abscissa denotes a frequency, and the ordinate denotes an echo signal intensity. As shown in a solid line frame in FIG. 7, when the 90° excitation pulse is applied in a state where its center frequency and the frequency bandwidth BW90 are set to the resonant frequency of a substance (M) to be imaged so as not to overlap the resonant frequency band of water, and thereafter, as shown in a dotted line frame in FIG. 7, the 180° refocus pulse is applied in a state where its center frequency and the frequency bandwidth BW180 are set so as to contain the resonant frequencies of the substance (M) and water, it is possible to acquire signals from the substance (M) while suppressing signals from water.

Figure 8:
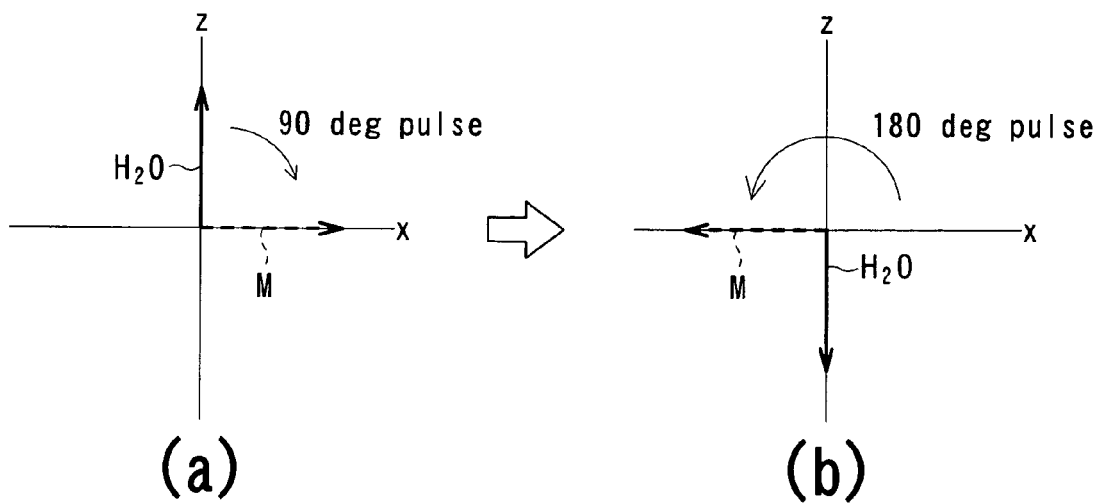
FIG. 8 is a diagram showing spin states of protons transitioned by the excitation and refocus in a frequency area shown in FIG. 7.

FIG. 8 is a diagram showing spin states of protons transitioned by the excitation and refocus in a frequency area shown in FIG. 7.

In FIG. 8(a) and 8(b), the ordinate axis z and abscissa axis x each denote a magnetization direction of proton spins. In a state where the proton spins in a water area and an area containing a substance (M) have been magnetized in the z-axis direction, when the 90° excitation pulse of which the center frequency and the frequency bandwidth BW90 has been set to the resonant frequency of substance (M) as shown in FIG. 7, is applied to a slice to be imaged, the protons in the area containing the substance (M) are excited by the 90° excitation pulse as shown in FIG. 8(a). Hence, the protons are inclined by 90° and magnetized in the x-axis direction. On the other hand, because the protons in the water area are subjected to no influence of the 90° excitation pulse, their magnetization direction still remains the z-axis direction.

Next, when the 180° refocus pulse of which the center frequency and frequency bandwidth BW180 has been set so as to cover the resonant frequencies of the substance (M) and water as shown in FIG. 7, is applied to the slice, the protons in the area containing the substance (M) are refocused by the 180° refocus pulse as shown in FIG. 8(b). Hence, protons are inclined by 180° and magnetized in the inversed direction on the x-axis. On the other hand, since the protons in the water area are refocused by the 180° refocus pulse, they are inclined by 180° and magnetized in the inversed direction on the z-axis.

As a result, echo signals occur from the substance (M) but not from water. This enables acquiring echo signals from the substance (M), with signals from water suppressed.

Figure 9:
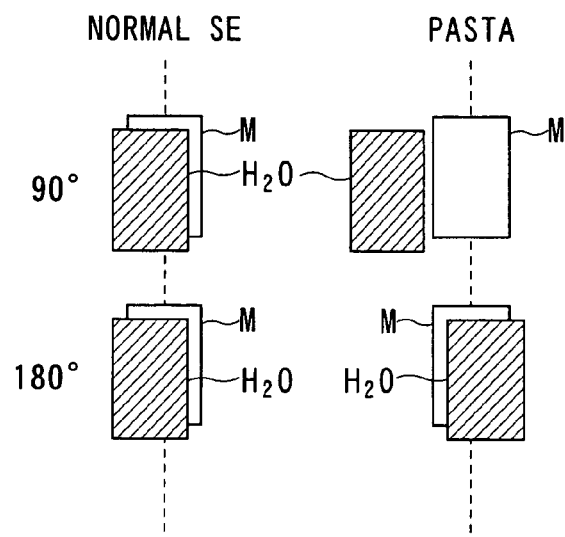
FIG. 9 is a diagram in which an area excited and refocused by the PASTA sequence shown in FIG. 5 is compared with an area excited and refocused by a normal SE sequence.

FIG. 9 is a diagram in which an area excited and refocused by the PASTA sequence shown in FIG. 5 is compared with an area excited and refocused by a normal SE sequence.

As shown in FIG. 9, in the normal SE sequence, both of a water area and an area containing a substance (M) in a selected slice are each excited and refocused by the 90° excitation pulse and 180° refocus pulse, respectively. In contrast, as can be seen from FIG. 6, in the PASTA sequence, although the area containing the substance (M) in the selected slice is excited by the 90° excitation pulse, the water area is excited outside the selected slice by the 90° excitation pulse. Thereafter, both of the water area and the area containing the substance (M) in the selected slice are each refocused by the 180° refocus pulse.

So far, the case where the substance (M) is imaged has been described, but when imaging of a breast implant is to be performed, imaging of water and silicone is required. It is, therefore, necessary that the center frequency and frequency bandwidth BW90 of the 90° excitation pulse are set to both of the resonant frequencies of silicone and water, independently, i.e., twice in total, by adjusting the center frequency of the 90° excitation pulse and magnetizing conditions in the PASTA sequence. However, between the resonant frequencies of water and silicone, the resonant frequency of fat exists in the vicinity of the resonant frequency of silicone. As a result, fat is also subjected to influences of the 90° excitation pulse and 180° refocus pulse, together with silicone.

Figure 10:
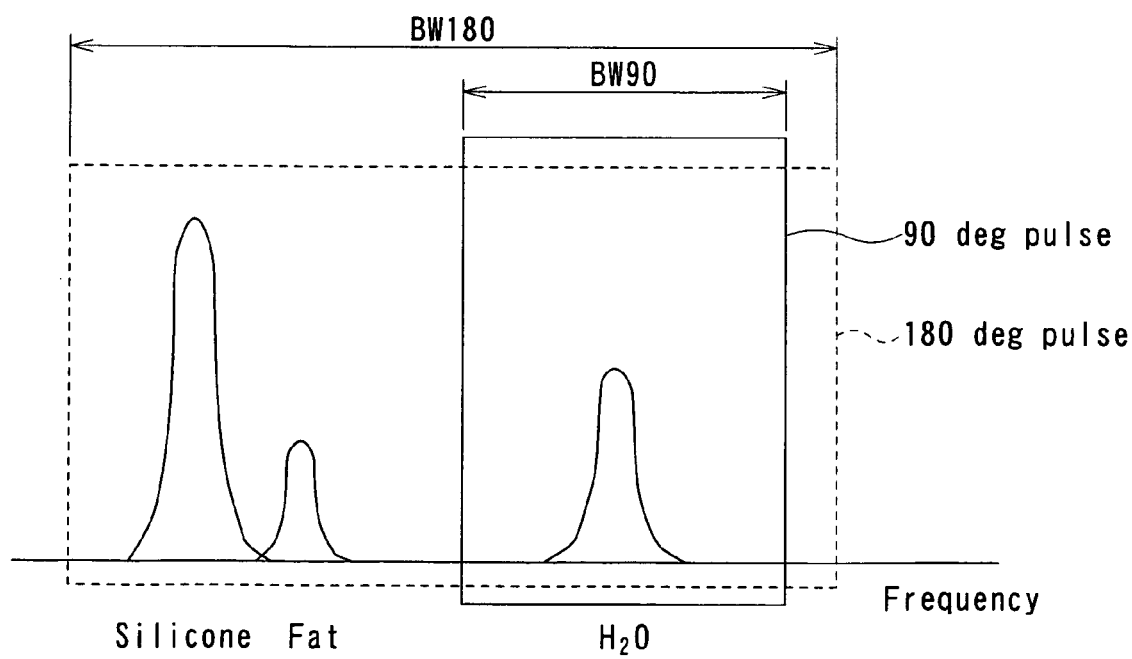
FIG. 10 is a diagram showing frequency areas that are excited and refocused by the execution of a scan by the PASTA sequence shown in FIG. 5 when water is excited.

FIG. 10 is a diagram showing frequency areas that are excited and refocused when water is excited by the execution of a scan by the PASTA sequence shown in FIG. 5.

In FIG. 10, the abscissa denotes a frequency, and the ordinate denotes an echo signal intensity. As shown in a solid line frame in FIG. 10, when the 90° excitation pulse is applied in a state where its center frequency and the frequency bandwidth BW90 are set to the resonant frequency of water so as not to overlap the resonant frequency bands of silicone and fat, and thereafter, as shown in a dotted line frame in FIG. 10, the 180° refocus pulse is applied in a state where its center frequency and the frequency bandwidth BW180 are set so as to contain the resonant frequencies of silicone, fat and water, it is possible to acquire signals from water while suppressing signals from silicone and fat.

Figure 11:
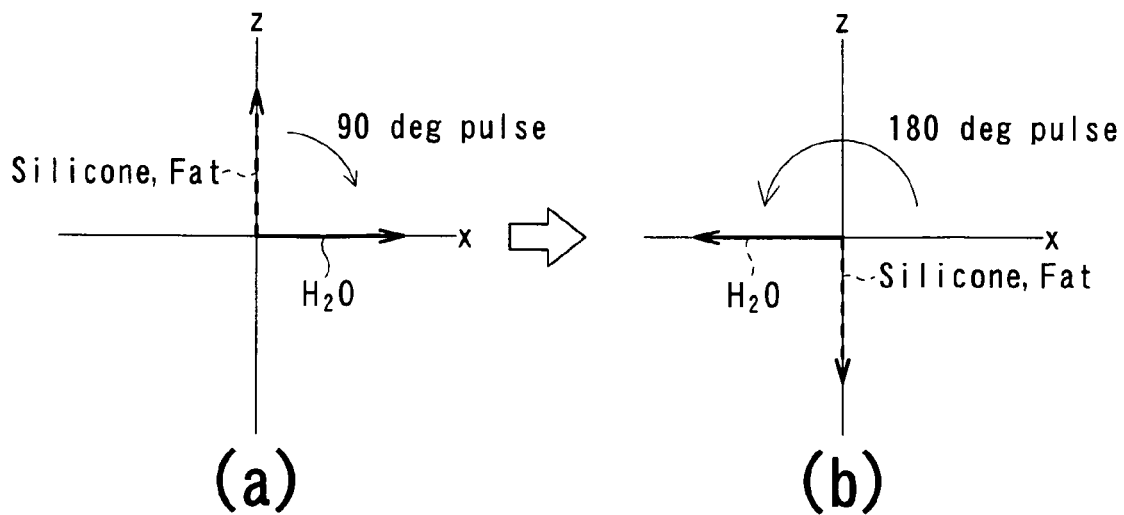
FIG. 11 is a diagram showing spin states of protons transitioned by the excitation and refocus in a frequency area shown in FIG. 10.

FIG. 11 is a diagram showing spin states of protons transitioned by the excitation and refocus in a frequency area shown in FIG. 10.

In FIG. 11(a) and 11(b), the ordinate axis z and abscissa axis x each denote a magnetization direction of proton spins. In a state where the proton spins in a water area, a silicone area and a fat area have been magnetized in the z-axis direction, when the 90° excitation pulse of which the center frequency and the frequency bandwidth BW90 has been set to the resonant frequency of water as shown in FIG. 10, is applied to a slice to be imaged, the protons in the water area are excited by the 90° excitation pulse as shown in FIG. 11(a). Hence, the protons are inclined by 90° and magnetized in the x-axis direction. On the other hand, because the protons in the silicone area and the fat area are subjected to no influence of the 90° excitation pulse, their magnetization direction still remains the z-axis direction.

Next, when the 180° refocus pulse of which the center frequency and frequency bandwidth BW180 has been set so as to cover the resonant frequencies of silicone, fat and water as shown in FIG. 10, is applied to the slice, the protons in the water area are refocused by the 180° refocus pulse as shown in FIG. 11(b). Hence, protons are inclined by 180° and magnetized in the inversed direction on the x-axis. On the other hand, since the protons in the silicone area and the fat area are refocused by the 180° refocus pulse, they are inclined by 180° and magnetized in the inversed direction on the z-axis.

As a result, echo signals occur from water but not from silicone and fat. This enables acquiring echo signals from water, with signals from silicone and fat suppressed.

Figure 12:
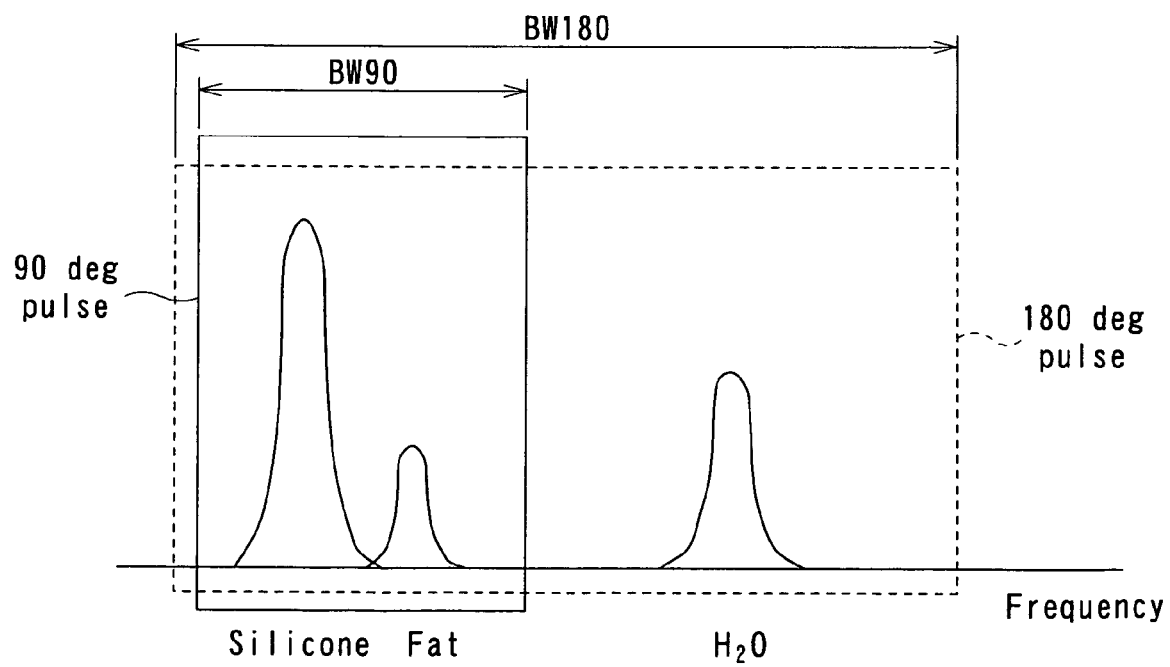
FIG. 12 is a diagram showing frequency areas that are excited and refocused when silicone is excited by the execution of a scan by the PASTA sequence shown in FIG. 5.

FIG. 12 is a diagram showing frequency areas that are excited and refocused when silicone is excited by the execution of a scan by the PASTA sequence shown in FIG. 5.

In FIG. 12, the abscissa denotes a frequency, and the ordinate denotes an echo signal intensity. As shown in a solid line frame in FIG. 12, when the 90° excitation pulse is applied in a state where its center frequency and the frequency bandwidth BW90 are set to the resonant frequencies of silicone and fat so as not to overlap the resonant frequency band of water, and thereafter, as shown in a dotted line frame in FIG. 12, the 180° refocus pulse is applied in a state where its center frequency and the frequency bandwidth BW180 are set so as to contain the resonant frequencies of silicone, fat and water, it is possible to acquire signals from silicone and fat while suppressing signals from water.

Figure 13:
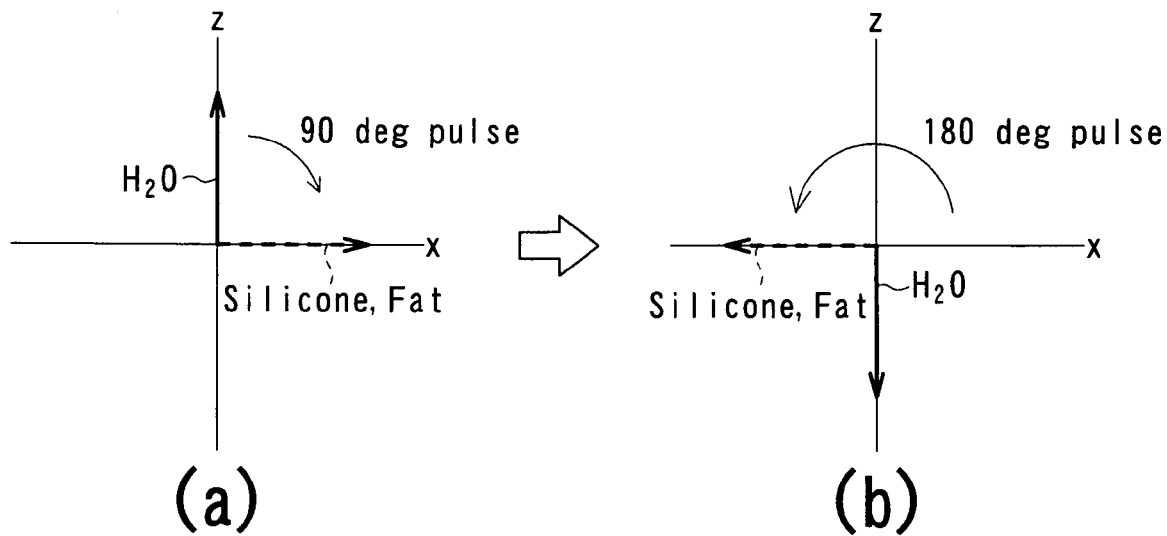
FIG. 13 is a diagram showing spin states of protons transitioned by the excitation and refocus in a frequency area shown in FIG. 12.

FIG. 13 is a diagram showing spin states of protons transitioned by the excitation and refocus in a frequency area shown in FIG. 12.

In FIG. 13(a) and 13(b), the ordinate axis z and abscissa axis x each denote a magnetization direction of proton spins. In a state where the proton spins in a water area, a silicone area and a fat area have been magnetized in the z-axis direction, when the 90° excitation pulse of which the center frequency and the frequency bandwidth BW90 has been set to the resonant frequencies of silicone and fat as shown in FIG. 12, is applied to a slice to be imaged, the protons in the silicone area and the fat area are excited by the 90° excitation pulse as shown in FIG. 13(a). Hence, the protons are inclined by 90° and magnetized in the x-axis direction. On the other hand, because the protons in the water area are subjected to no influence of the 90° excitation pulse, their magnetization direction still remains the z-axis direction.

Next, when the 180° refocus pulse of which the center frequency and frequency bandwidth BW180 has been set so as to cover the resonant frequencies of silicone, fat and water as shown in FIG. 12, is applied to the slice, the protons in the silicone area and the fat area are refocused by the 180° refocus pulse as shown in FIG. 13(*b*). Hence, protons are inclined by 180° and magnetized in the inversed direction on the x-axis. On the other hand, since the protons in the water area are refocused by the 180° refocus pulse, they are inclined by 180° and magnetized in the inversed direction on the z-axis.

As a result, echo signals occur from silicone and fat but not from water. This enables acquiring echo signals from silicone and fat, with signals from water suppressed.

Because the relative chemical shift between fat and silicone is small as described above, it may be difficult to excite only one out of fat and silicone merely by adjusting magnetizing conditions such as the frequency bandwidth BW90 of 90° excitation pulse and its center frequency. Such being the case, the pulse sequence can also be set so that a fat saturation pulse is applied as a pre-pulse in order to suppress signals from fat.

Figure 14:
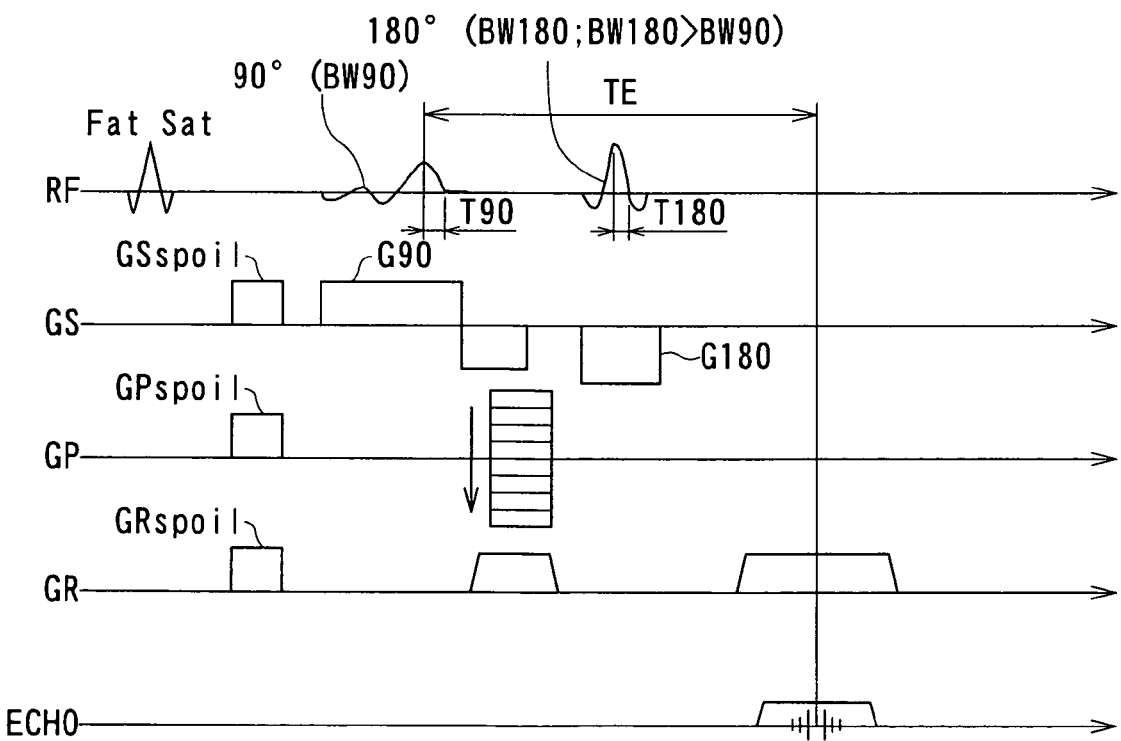
FIG. 14 is a diagram of a sequence obtained by adding fat saturation pulse as a pre-pulse to the PASTA sequence shown in FIG. 15.
Figures 15, 16:
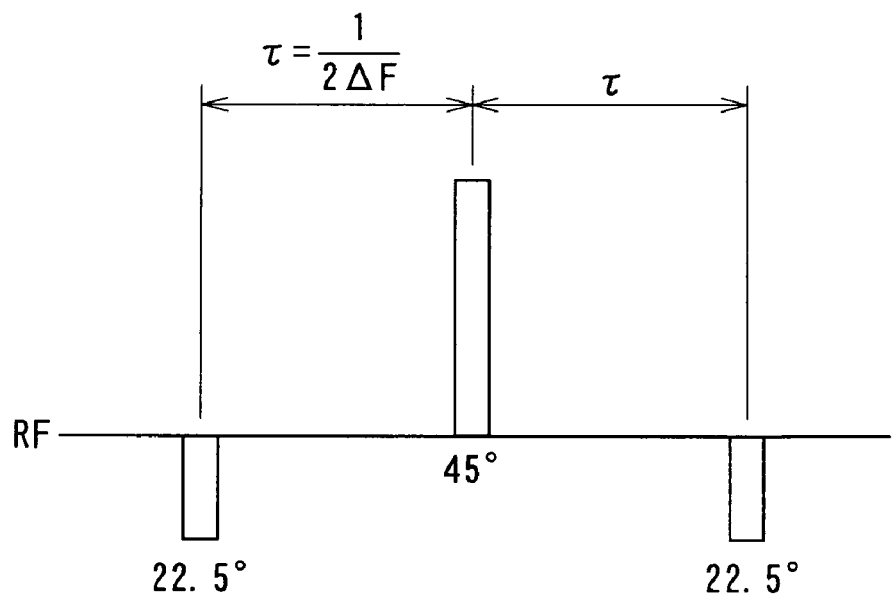
FIG. 15 is a diagram of a sequence obtained by adding fat saturation pulse as a pre-pulse to the PASTA sequence shown in FIG. 15.
FIG. 16 is a diagram explaining a setting method for an imaging condition in the imaging condition setting unit shown in FIG. 2 when performing molecular imaging using a sequence involving the application of 1:2:1-binomial pulse.

FIG. 14 is a diagram of a sequence obtained by adding fat saturation pulse as a pre-pulse to the PASTA sequence shown in FIG. 15.

In FIG. 14, reference character RF denotes a RF signal to be transmitted to an imaging area. Reference characters GS, GP, GR, and ECHO, respectively, denote a gradient magnetic field for slice selection, a gradient magnetic field for phase encode, a gradient magnetic field for readout, and a echo signal.

As shown in FIG. 14, the pulse sequence can be set so that a fat saturation pulse is applied as a pre-pulse, prior to the application of a 90° excitation pulse. When applying the fat saturation pulse, spoiler pulses GSspoil, GPspoil, and GRspoil, respectively, are applied to the gradient magnetic field GS for slice selection, the gradient magnetic field GP for phase encode, and the gradient magnetic field GR for readout, after the application of the fat suppression pulse.

The substance to be excited and/or the presence/absence of a fat saturation pulse as described above can be defined as an imaging protocol. Defining the imaging protocols allows setting a pulse sequence in the imaging condition setting unit 48, only by the operator selecting an imaging protocol for an imaging purpose by an operation of the input device 33.

FIG. 15 is a table showing an example of imaging protocol that can be designated in the imaging condition setting unit 48 shown in FIG. 2, and substances that can be imaged by respective imaging protocols.

For example, as shown in (1) in FIG. 15, the PASTA sequence wherein the center frequency and frequency bandwidth BW90 of the 90° excitation pulse are set to the resonant frequency of water, and wherein the sequence of an imaging portion has been made the FSE sequence, can be set as an imaging protocol FSE+15_pasta. Also, as shown in (2), the PASTA sequence in which the center frequency and frequency bandwidth BW90 of the 90° excitation pulse are set to the resonant frequency of silicone, and the sequence of the imaging portion has been made the FSE sequence, can be set as an imaging protocol FSE+15_pastaSi without FatSat. Furthermore, as shown in (3), the PASTA sequence in which the center frequency and frequency bandwidth BW90 of the 90° excitation pulse are set to the resonant frequency of silicone, and the sequence of the imaging portion has been made the FSE sequence, and which involves the application of a fat saturation pulse, can be set as an imaging protocol FSE+15_pastaSi with FatSat.

Upon execution of the imaging protocol (1) FSE+15_pasta, signals from fat and silicone are suppressed, which allows a water image to be reconstructed by acquiring echo signals from water and saline. Upon execution of the imaging protocol (2) FSE+15_pastaSi without FatSat, signals from water and saline are suppressed, which allows an image with fat and silicone imaged to be reconstructed by acquiring echo signals from fat and silicone. Upon execution of the imaging protocol (3) FSE+15_pastaSi with FatSat, signals from water and saline are suppressed by chemical shift imaging, and simultaneously signals from fat are suppressed by a fat saturation pulse, which allows a silicone image to be reconstructed by acquiring echo signals from silicone.

Therefore, examination of a breast implant by performing scans using the above-described imaging protocols in combination, enables identification as to whether the implant is constituted of silicone or saline, and further enables detection of a leakage of silicone. Specifically, performing a scan by the imaging protocol FSE+15_pasta and a scan by the imaging protocol FSE+15_pastaSi without FatSat allows identification as to whether the implant is constituted of silicone or saline by comparing the images obtained by the both scans. On the other hand, performing a scan by the imaging protocol FSE+15_pastaSi without FatSat and a scan by the imaging protocol FSE+15_pastaSi with FatSat allows detection of a leakage of silicone by comparing images obtained by the both scans.

Next, the molecular imaging by a sequence using binomial pulses will be described. The binomial pulses are component pulses that are divided in a proportion based on a binomial distribution, such as 1:1, 1:2:1, 1:3:3:1, and it is known that the fat suppression effect is improved as the number of divisions increases. Adjustment of the time of $\tau$ length of the binomial pulses also allows chemical imaging of a specified substance. Use of binomial pulses facilitates the control of the $\tau$ length.

FIG. 16 is a diagram explaining a setting method for an imaging condition in the imaging condition setting unit 48 shown in FIG. 2 when performing molecular imaging using a sequence involving the application of 1:2:1-binomial pulse.

As shown in FIG. 16, the 1:2:1-binomial pulses are a pulse train that is arranged so that three component pulses: a 22.5° excitation pulse, a 45° excitation pulse, and a 22.5° excitation pulse, are sequentially applied with the passage of the time of $\tau$ length. The 45° excitation pulse is made opposite in polarity to the two 22.5° excitation pulses.

Adjustment of the time of $\tau$ length of the 1:2:1-binomial pulses in accordance with the chemical shift value of a substance to be imaged, enables molecular imaging. Specifically, if the phase of magnetization of the substance to be imaged becomes an opposite phase after the time of $\tau$ length by a phase shift of the magnetization depending on the chemical shift values of the substance, echo signals can be selectively acquired from the substance. Hence, it is advisable to set a $\tau$ length from the chemical shift value $\Delta F$ of the substance, using the following expression (6).

$$\tau = 1/(2\Delta F) \quad (6)$$

For example, when echo signals from water are acquired while suppressing fat, the time of $\tau$ length becomes $\tau=2.17$ [ms], from a chemical shift value $\Delta F=230$ Hz of fat with respect to water, using the expression (6). Also, for example, when the chemical shift value of a drug to be imaged is $\Delta F=150$ Hz, if the time of $\tau$ length is set to $\tau=3.33$ [ms], it is possible to selectively acquire signals from the drug while suppressing signals from water, and generate an image of the drug.

Figure 17:
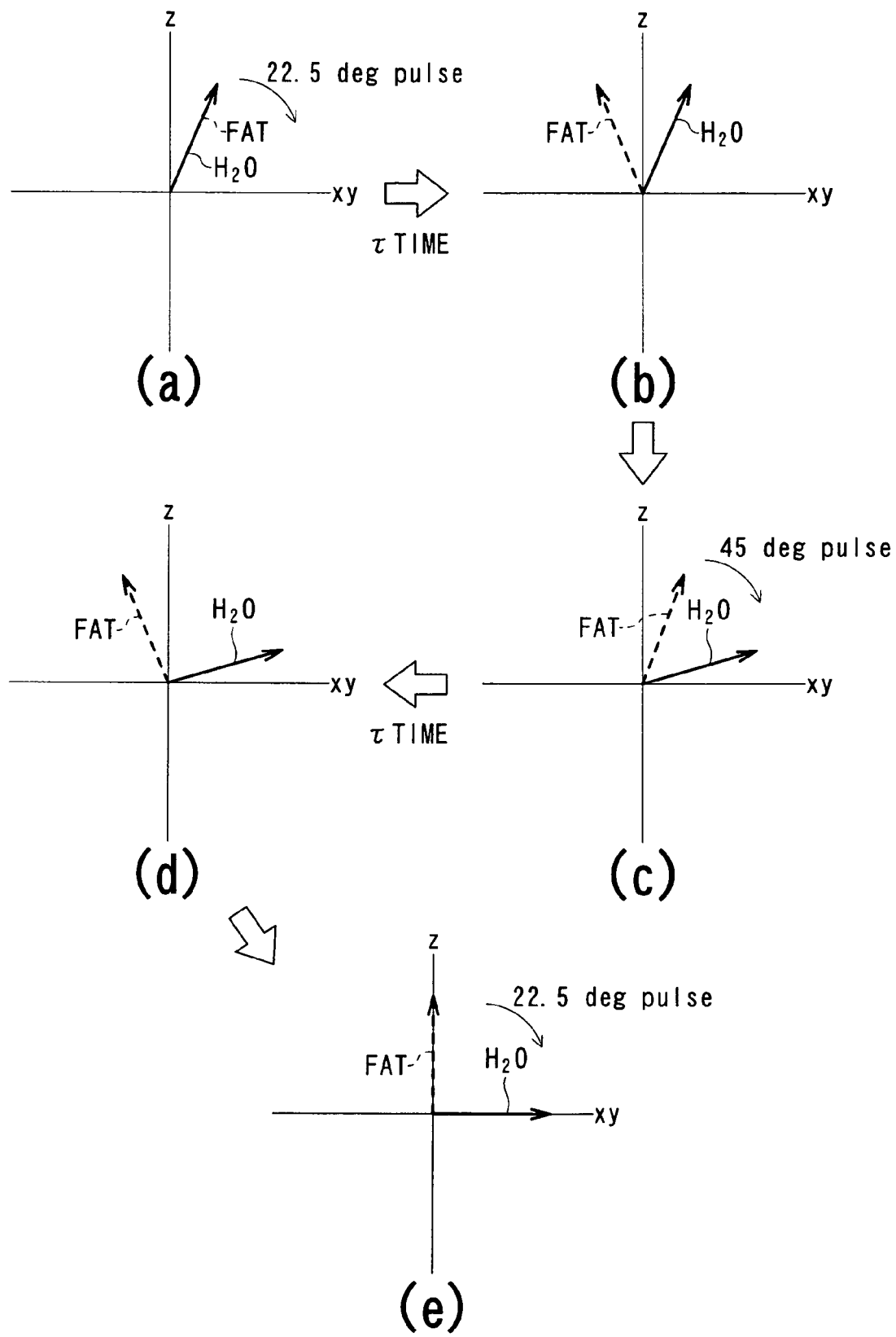
FIG. 17 is a diagram showing transitions of spin states of protons when acquiring signals from water while suppressing signals from fat using the 1:2:1-binomial pulse shown in FIG. 16.

FIG. 17 is a diagram showing transitions of spin states of protons when acquiring signals from water while suppressing signals from fat using the 1:2:1-binomial pulse shown in FIG. 16.

In FIG. 17(a),(b),(c),(d) and (e), the ordinate denotes z-axis direction component of proton spins, and the abscissa denotes x-y plane component thereof. Upon applying the 1:2:1-binomial pulses, as shown in FIG. 16, in which a τ length is set so that signals from water are acquired while suppressing signals from fat in a state where the proton spins in the water area and fat area have been magnetized in the Z-axis direction, the proton spins in the water area and the fat area are each excited by the first 22.5° excitation pulse. As a result, the proton spins in the water area and the fat area are each magnetized in the direction inclined from the z-axis toward an xy-axis by 22.5°, as shown in FIG. 17(a).

Then, after the lapse of a X time, the phase of magnetization of the proton spins in the fat area is displaced, and takes an direction inclined from the z-axis toward the xy-axis by −22.5°, as shown in FIG. 17(b).

Here, upon applying the second 45° excitation pulse, the magnetization direction of the proton spins in the fat area is shifted in a clockwise direction by 45° to become a direction inclined from the z-axis toward the xy-axis by 22.5°, as shown in FIG. 17(c). On the other hand, the magnetization direction of the proton spins in the water area is shifted in a clockwise direction by 45° to become a direction inclined from the z-axis toward the xy-axis by 67.5°.

Then, after the lapse of a τ time, the phase of magnetization of the proton spins in the fat area is displaced, and takes a direction inclined from the z-axis toward the xy-axis by −22.5°, as shown in FIG. 17(d).

Next, upon applying the third 22.5° excitation pulse, the magnetization direction of the proton spins in the fat area is shifted in a clockwise direction by 22.5° and coincides with the z-axis direction, as shown in FIG. 17(e). On the other hand, the magnetization direction of the proton spins in the water area is shifted in a clockwise direction by 22.5°, and coincides with the xy-axis direction.

As a result, echo signals occur from water but not from fat. This enables acquiring echo signals from water, with signals from fat suppressed.

Figure 18:
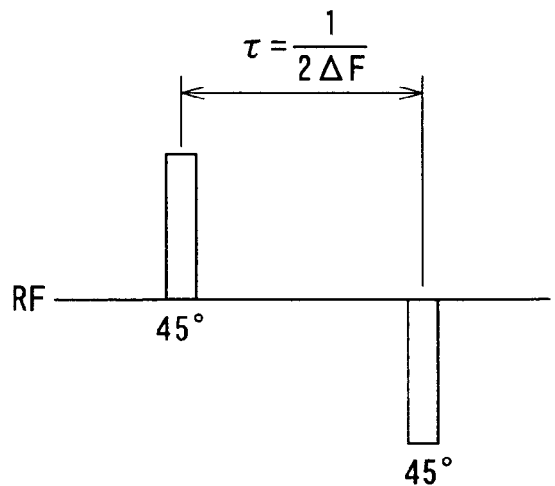
FIG. 18 is a diagram explaining a setting method for an imaging condition in the imaging condition setting unit shown in FIG. 2 when performing molecular imaging using a sequence involving the application of 1:1-binomial pulse.

FIG. 18 is a diagram explaining a setting method for an imaging condition in the imaging condition setting unit 48 shown in FIG. 2 when performing molecular imaging using a sequence involving the application of 1:1-binomial pulse.

As shown in FIG. 18, the 1:1-binomial pulses is a pulse train that is arranged so that two 45° excitation pulses are sequentially applied with the passage of the time of τ length. The two 45° excitation pulses are made opposite in polarity to each other. Based on the same principle as that in the case where molecular imaging is performed using the 1:2:1-binomial pulses, the setting of the time of τ length of the 1:1-binomial pulses based on the expression (6) makes it possible to perform molecular imaging using the 1:1-binomial pulses.

Figure 19:
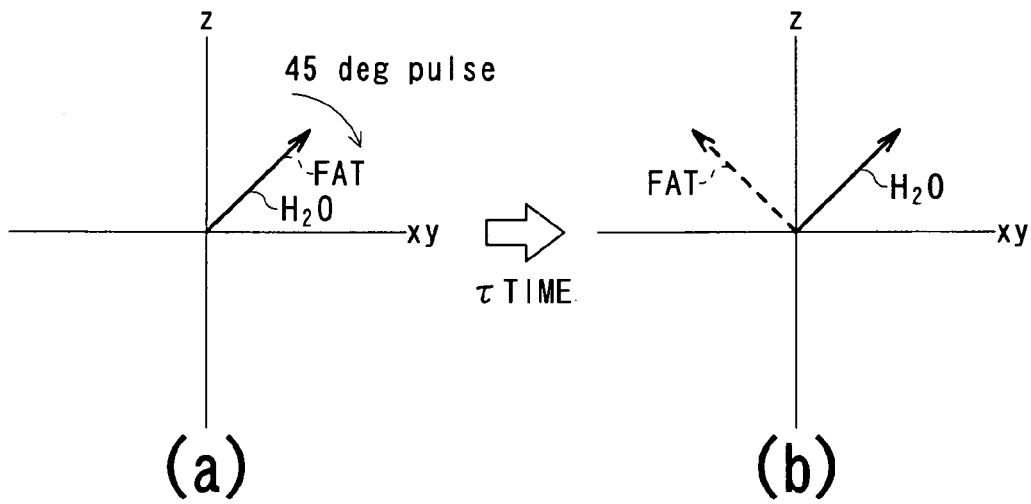
FIG. 19 is a diagram showing transitions of spin states of protons when acquiring signals from water while suppressing signals from fat using the 1:1-binomial pulse shown in FIG. 18.
Figure 19:
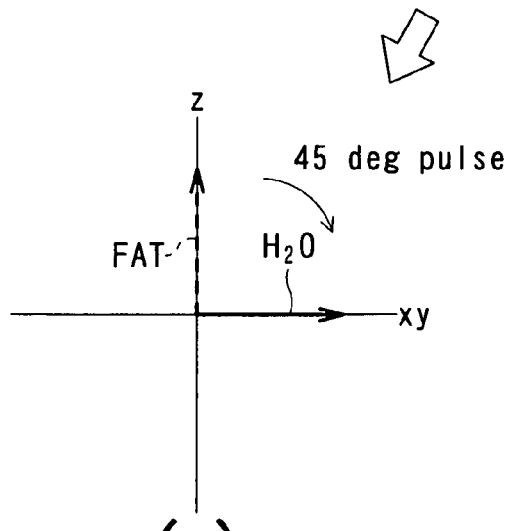

FIG. 19 is a diagram showing transitions of spin states of protons when acquiring signals from water while suppressing signals from fat using the 1:1-binomial pulse shown in FIG. 18.

In FIG. 19(a),(b) and (c), the ordinate denotes z-axis direction component of proton spins, and the abscissa denotes x-y plane component thereof. Upon applying the 1:1 1-binomial pulses, as shown in FIG. 18, in which a τ length is set so that signals from water are acquired while suppressing signals from fat in a state where the proton spins in the water area and fat area have been magnetized in the Z-axis direction, the proton spins in the water area and the fat area are each excited by the first 45° excitation pulse. As a result, the proton spins in the water area and the fat area are each magnetized in the direction inclined from the z-axis toward an xy-axis by 45°, as shown in FIG. 19(a).

Then, after the lapse of a τ time, the phase of magnetization of the proton spins in the fat area is displaced, and takes an direction inclined from the z-axis toward the xy-axis by −45°, as shown in FIG. 19(b).

Next, upon applying the second 45° excitation pulse, the magnetization direction of the proton spins in the fat area is shifted in a clockwise direction by 45° and coincides with the z-axis direction, as shown in FIG. 19(c). On the other hand, the magnetization direction of the proton spins in the water area is shifted in a clockwise direction by 45°, and coincides with the xy-axis direction.

As a result, echo signals occur from water but not from fat. This enables acquiring echo signals from water, with signals from fat suppressed.

Next, molecular imaging by a sequence using the three-point Dixon sequence will be described.

The three-point Dixon method is a method in which, in addition to the normal 180° refocus pulse in the SE method, a π pulse and a −π pulse, which are, respectively, shifted by ±τ length time from the 180° refocus pulse in application time, are applied. The time of τ time is set so that the transverse magnetization phases of water and a specified substance become completely opposite to each other by the π pulse and the −π pulse after the lapse of a time TE. By performing an addition and subtraction between an image data acquired so that the transverse magnetization phases of water and the specified substance become equal to each other, and an image data acquired so that their transverse magnetization phases become completely opposite to each other, it is possible to separately obtain a water image and an image with the specified substance enhanced.

Figure 20:
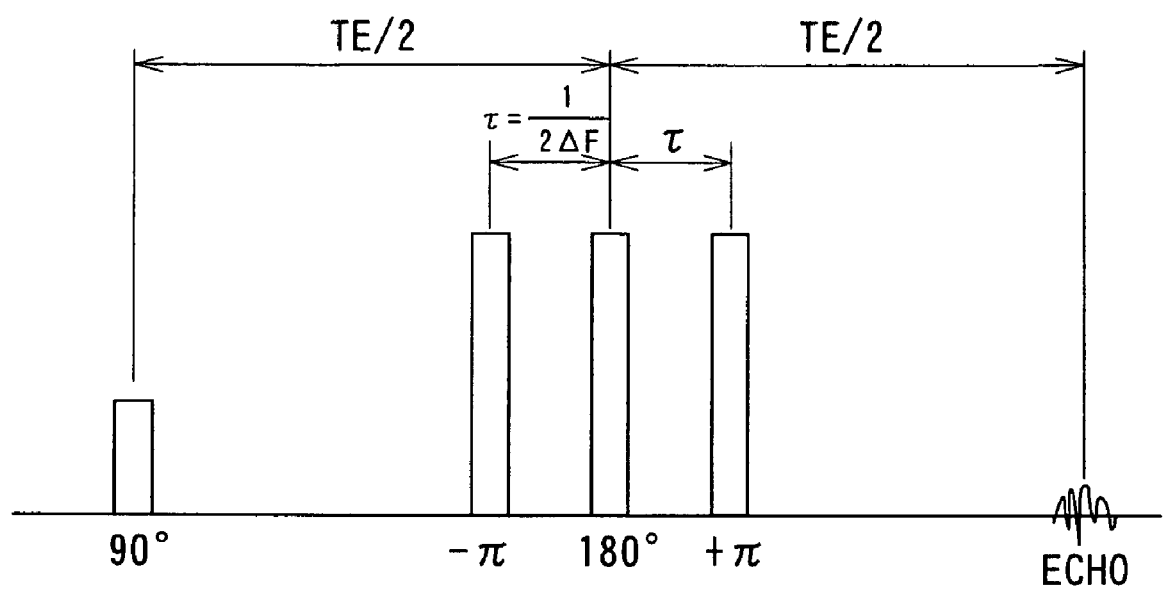
FIG. 20 is a diagram explaining a setting method for an imaging condition in the imaging condition setting unit shown in FIG. 2 when performing molecular imaging using the three-point Dixson sequence.

FIG. 20 is a diagram explaining a setting method for an imaging condition in the imaging condition setting unit 48 shown in FIG. 2 when performing molecular imaging using the three-point Dixson sequence.

As shown in FIG. 20, in the three-point Dixson sequence, while an echo signal is acquired at a time TE after the application of a 90° excitation pulse. A 180° refocus pulse is applied at time TE/2 after the application of the 90° excitation pulse. Also, a −π pulse is applied at the τ time before the application of the 180° excitation pulse, and a +π pulse is applied at the τ time after the application of the 180° excitation pulse. Setting this τ length time of the three-point Dixon sequence based on a chemical shift value of a substance in accordance with the expression (6) allows molecular imaging to be performed.

For example, when the chemical shift value of a drug to be imaged with respect to water is ΔF=3.0 ppm, τ length time can be set based on the expression (6). When a static magnetic field intensity is 1.5 T, the chemical shift value ΔF of the drug is determined as shown in the following expression (7-1), so that the time of τ length can be determined by the following expression (7-2).

$$\Delta F=3.0\ [\text{ppm}]=192\ [\text{Hz}]\ (\because 1\ \text{ppm}=64\ \text{Hz}) \tag{7-1}$$

$$\tau=1/(2\cdot 192)\ [\text{s}]=2.6\ [\text{ms}] \tag{7-2}$$

The imaging condition setting unit 48 for setting imaging conditions as described above includes a function of designating a single or a plurality of substances to be subjected to chemical shift imaging, a function of setting the center frequency of an excitation pulse to the resonant frequency of the designated substance, a function of adjusting magnetizing conditions such as a τ length in conformance with the designated substance, and a function of designating the presence/absence of the application of a fat saturation pulse.

In order to improve convenience of the operator, the imaging condition setting unit 48 further includes a function of setting imaging conditions for obtaining an image of an intended substance without the need for knowledge about chemical shift, and a function of automatically setting the center frequencies of excitation pulses to the resonant frequencies of a plurality of substances respectively by a single time shimming and a single time designating operation of substances to be subjected to chemical shift imaging. These functions can be modally performed by selecting an automatic imaging condition setting mode and automatic frequency setting mode.

To that end, the imaging condition setting unit 48 includes a substance designation unit 52, a first frequency setting unit 53, a second frequency setting unit 54, a magnetizing condition setting unit 55 and a fat saturation designating unit 56. Also, the imaging condition setting unit 48 is configured to cause the display unit 34 to display a setting screen for setting imaging conditions utilizing a graphical user interface (GUI), and to set the imaging conditions by an operation of the input device 33.

The substance designation unit 52 includes a function of designating substances to be subjected to chemical shift imaging in accordance with instruction information from the input device 33, and a function of providing identification information about the designated substance to the first frequency setting unit 53, the second frequency setting unit 54, and the magnetizing condition setting unit 55. Here, not only a single substance but also a plurality of substances can be designated for chemical shift imaging. When a plurality of substances is subjected to chemical shift imaging respectively, the order of imaging is also designated. The substances to be designated include water, fat, silicone, saline, and a substance, such as a drug, of which the chemical shift value is known.

The designation of a substance to be subjected to chemical shift imaging is performed by using a substance name or a chemical shift value, and besides, by selecting an imaging protocol (sequence) intended for chemical shift imaging of the specified substance as shown in FIG. 15. In addition, the substance to be subjected to chemical shift imaging can be designated also by instructing the substance designation unit 52 for an imaging purpose by an operation of the input device 33. For example, instruction for checking whether a breast implant is constituted of silicone or saline as an imaging purpose allows the substances to be subjected to chemical shift imaging to be designated as silicone, and water or saline. Furthermore, for example, instructing for detecting a leakage of silicone from a breast implant as an imaging purpose allows the substances to be subjected to chemical shift imaging to be designated as fat and silicone.

Identification information about the substance to be subjected to chemical shift imaging performed at the first time is provided from the substance designation unit 52 to the first frequency setting unit 53. Then, identification information about substances to be subjected to chemical shift imagings that are performed at the second and subsequent times, and imaging order information showing the order of imagings are provided from the substance designation unit 52 to the second frequency setting unit 54. Furthermore, identification information about all substances to be subjected to chemical shift imagings and imaging order information showing the order of imagings are provided from the substance designation unit 52 to the magnetizing condition setting unit 55.

The first frequency setting unit 53 is configured so that, when it received the identification information about the substance to be a target for chemical shift imaging from the substance designation unit 52, it performs the function of acquiring the resonant frequency of the corresponding substance from the resonant frequency acquiring unit 47, and performs the function of setting the center frequency of excitation pulse in the pulse sequence used for the chemical shift imaging for the first-time substance to the resonant frequency of the first-time substance.

The second frequency setting unit 54 is configured so that, when it received the identification information about the substances to be subjected to chemical shift imagings performed at the second and subsequent times and the imaging order information from the substance designation unit 52, it performs the function of acquiring the resonant frequencies of the corresponding substances from the resonant frequency acquiring unit 47, and performs the function of setting the center frequency of respective excitation pulses in the pulse sequences to be performed at the second and subsequent times following the pulse sequence produced by the first frequency setting unit 53 to the resonant frequencies of substances having corresponding orders respectively.

That is, the imaging condition setting unit 48 is configured so that, as long as the operator once designates substances to be subjected to chemical shift imaging, even when two or more substances are designated, the center frequencies of the respective excitation pulses are automatically changed into the resonant frequencies of corresponding substances by the second frequency setting unit 54. Hence, when three substances to be subjected to chemical shift imaging are designated, the center frequency of the excitation pulse is automatically changed into the resonant frequencies of corresponding substances by the second frequency setting unit 54 twice in total.

The magnetizing condition setting unit 55 is configured so that, when it received identification information and imaging order information about substances to be subjected to chemical shift imaging from the substance designation unit 52, it performs the function of setting magnetizing conditions, such as the respective frequency bandwidths BW90 and BW180, the respective τ lengths τ90 and τ180 of the 90° excitation pulse and the 180° refocus pulse, and the gradient magnetic fields G90 and G180 for slice selection to be applied along with the 90° excitation pulse and the 180° refocus pulse, respectively, so that the resonant frequencies of substances to be suppressed in the PASTA sequence and the frequency bandwidth BW90 of the 90° excitation pulse do not overlap each other; it performs the function of setting the time of τ length constituting a magnetizing condition for the binomial pulses or Three-point Dixon sequence in conformance with the chemical shift value of a substance to be imaged; and it performs the function of reflecting the set magnetizing conditions on the pulse sequence. Also, the magnetizing condition setting unit 55 is configured to acquire the resonant frequency of a substance necessary for setting the magnetizing conditions from the resonant frequency acquiring unit 47.

The fat saturation designating unit 56 is configures so that it performs the function of determining the presence/absence of the application of a fat saturation pulse per imaging of each substance in accordance with instruction information from the input device 33, and so that, when it was determined that the fat saturation pulse is to be applied, it performs the function of adding fat saturation pulse to a pulse sequence for performing corresponding chemical shift imaging.

The pulse sequences for respective substances, produced by the above-described elements are sequentially provided from the imaging condition setting unit 48 to the sequence controller controlling unit 40 in accordance with the imaging order. Furthermore, as imaging conditions, screen information for setting pulse sequences and/or screen information for instructing for an acquiring method or correction of a resonant frequency are provided to the display unit 34 from the imaging condition setting unit 48 and the resonant frequency acquiring unit 47, and a setting screen for chemical shift imaging is displayed on the display unit 34 as an interface.

Figure 21:
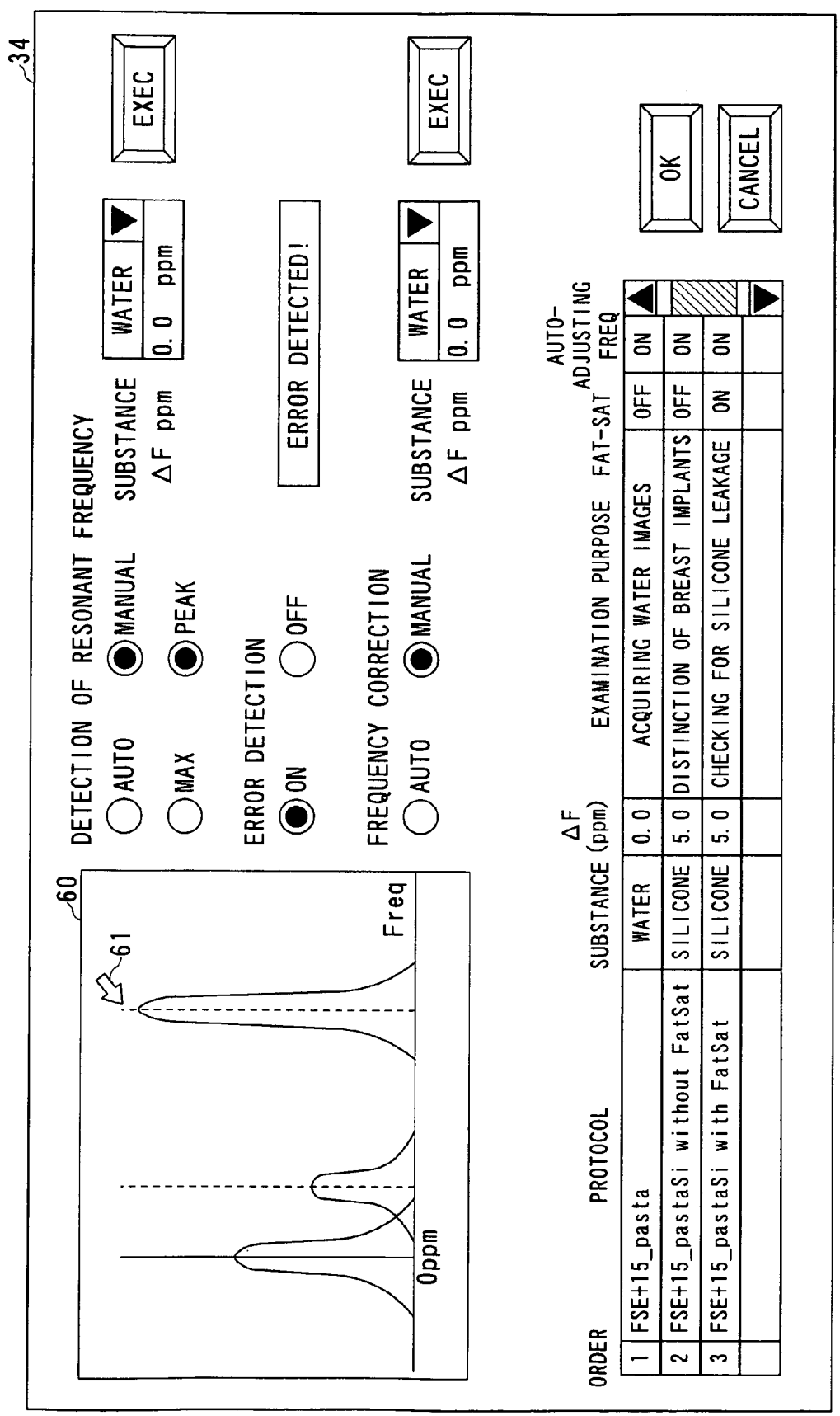
FIG. 21 is a diagram showing an example of a setting screen for chemical shift imaging displayed on the display unit shown in FIG. 2.

FIG. 21 is a diagram showing an example of a setting screen for chemical shift imaging displayed on the display unit 34 shown in FIG. 2.

As shown in FIG. 21, the setting screen for chemical shift imaging is displayed on the display unit 34. The setting screen displays a frequency spectrum 60 acquired by the frequency spectrum acquiring unit 49.

It can be designated whether the detection of a resonant frequency is to be performed automatically or manually, by an operation of the input device 33 such as a mouse or a pointer. Also, the substance showing a resonant frequency to be detected can be selected or inputted as a substance name or a chemical shift value. Furthermore, it can also be designated whether a resonant frequency is to be acquired by detecting the peak in a frequency spectrum or the maximum value therein.

The changeover of operation of automatic error detection for checking whether a detected resonant frequency has been erroneously recognized, to a manual detection operation, can be designated by an operation of the input device 33. For example, in a state where the error detecting function of a resonant frequency is turned on, when the operator manually recognizes the peak indicated by a solid line on the higher frequency side as the resonant frequency of water out of peaks detected from the frequency spectrum 60 and indicated by a plurality of dotted lines as shown in the sample in FIG. 21, a message "ERROR DETECTED!" is displayed by the error detecting function.

In order to correct such a detection error of a resonant frequency, correction of the resonant frequency can be automatically or manually performed by operating the input device 33. For example, in a state where the name of a substance showing the resonant frequency after the correction is set to water, when the peak on the lower frequency side in the frequency spectrum 60 is selected by moving an instruction character 61 by an operation of the input device 33 such as the mouse or a pointer, the resonant frequency of water can be correctly recognized.

Moreover, a setting column of imaging conditions is displayed in a lower portion of the setting screen. By an operation of the input device 33, the operator can indicate an imaging order, imaging protocols, substances to be subjected to chemical imaging, chemical shift values, imaging purposes, presence/absence of a fat saturation pulse, and in addition, whether an automatic setting of the center frequency of the excitation pulse is performed. In addition, when the imaging protocol or the imaging purpose is inputted, other imaging conditions may be automatically displayed.

Furthermore, magnetizing conditions such as the time of τ length and the like may be displayed on the setting screen, for reference.

Next, description is made of operations and effects of the magnetic resonance imaging apparatus 20, taking the case where a breast implant is examined using the PASTA sequence, as an example.

Figure 22:
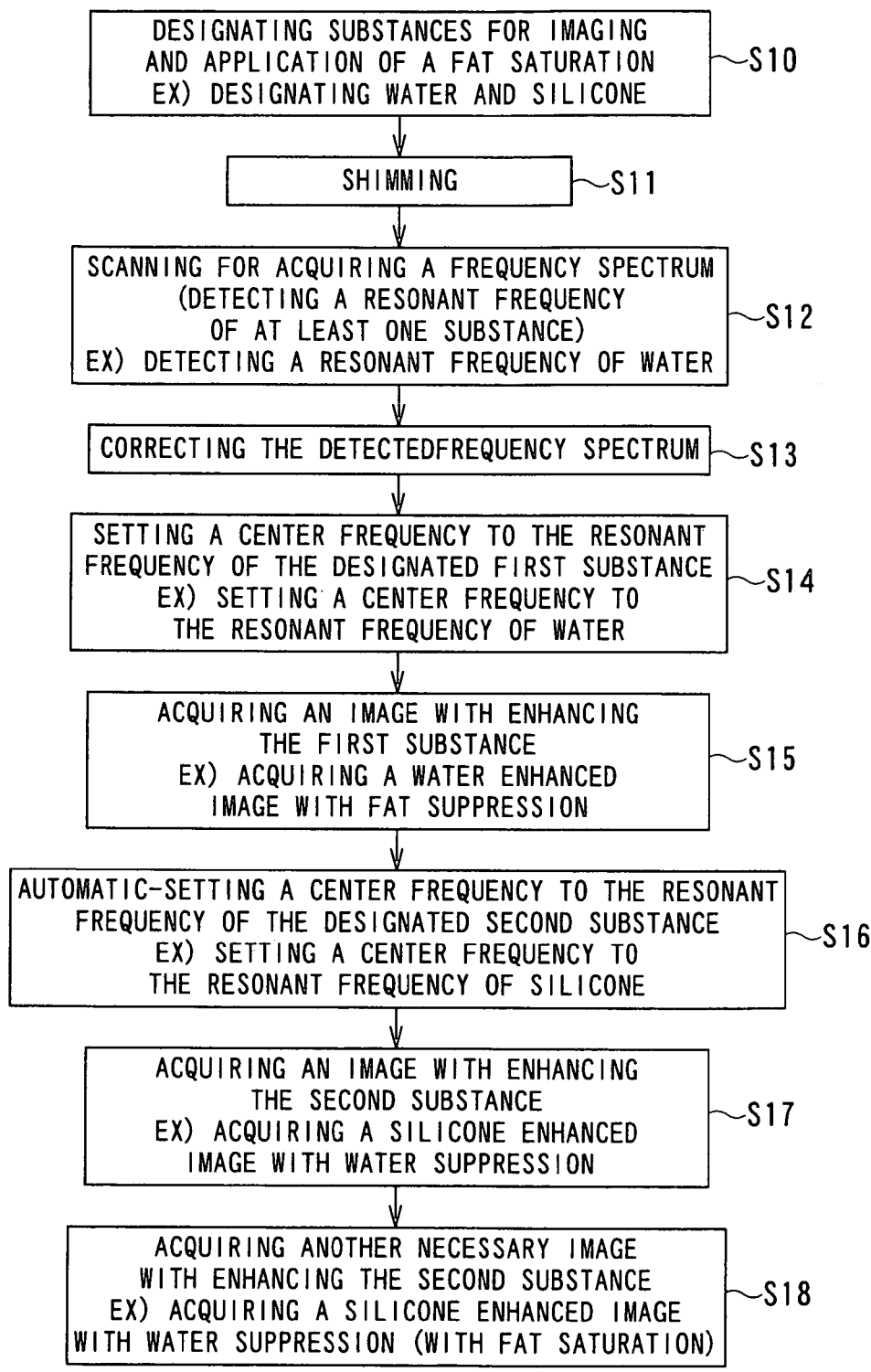
FIG. 22 is a flowchart showing an example of flow for breast imaging using chemical shifts by the magnetic resonance imaging apparatus shown in FIG. 1.
Figure 23:
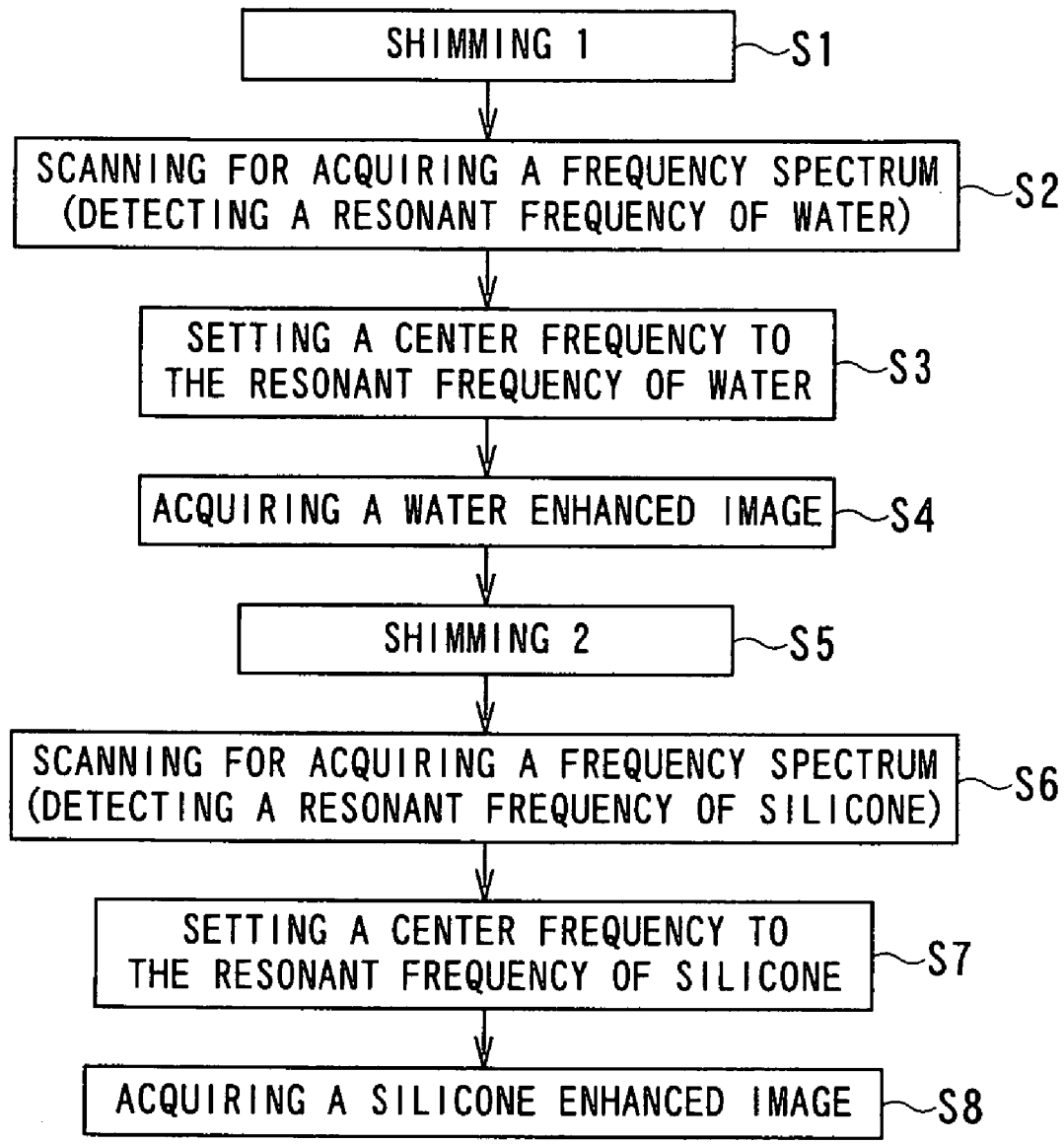
FIG. 23 is a flowchart showing a conventional procedure of a chemical shift imaging of water and silicone.

FIG. 22 is a flowchart showing an example of flow for breast imaging using chemical shifts by the magnetic resonance imaging apparatus 20 shown in FIG. 1. Reference numerals having numbers added to reference symbol S denote steps in the flowchart shown in FIG. 22.

First, in step S10, substances to be subjected to chemical shift imaging are designated by an operation of the input device 33 by the operator. In the imaging of a breast implant, imagings of water or saline, and silicone are required. Also, when the silicone leakage is to be detected, a silicone image with water and fat suppressed is required.

Such being the case, for example, the operator selects the three imaging protocols: FSE+15_pasta, FSE+15_pastaSi without FatSat, and FSE+15_pastaSi with FatSat shown in FIG. 15 by an operation of the input device 33, and sets an imaging order so that the imaging by the FSE+15_pastaSi without FatSat is performed after the imaging by the FSE+15_pasta, and the imaging by the FSE+15_pastaSi with FatSat is performed after the imaging by the FSE+15_pastaSi without FatSat. The operator also selects a frequency automatic setting mode by an operation of the input device 33.

Thereupon, the substance to be subjected to chemical shift imaging performed at the first time is set to water, and the substances to be subjected to chemical shift imagings performed at the second and third times are each set to silicone by the substance designation unit 52. In the chemical shift imaging performed at the third time, application of a fat saturation pulse is designated by the fat saturation designating unit 56.

Note that, the operator may designate silicone or water as substance names or a chemical shift values, or else as imaging purposes. Also, the designation of the necessity/unnecessity of fat saturation may be directly performed by an operation of the input unit 33.

Then, information that a water image is acquired at the first-time scan by the RASTA sequence is provided from the substance designation unit 52 to the first frequency setting unit 53. Also, information that a silicone image is acquired at each of the second and third scans by the RASTA sequences is provided from the substance designation unit 52 to the second frequency setting unit 54. Moreover, the information that a water image is acquired at the first-time scan by the RASTA sequence, and that a silicone image is acquired at each of the second and third scans by the RASTA sequences is provided from the substance designation unit 52 to the magnetizing condition setting unit 55.

Next, in step S11, shimming is performed by the operator, and thereby the uniformity of the static magnetic field intensity is adjusted. Specifically, when the operator provides instruction information from the input unit 33 to the shim coil power supply 28 through the shimming condition setting unit 46, the shimming condition setting unit 46 provides a control signal to the shim coil power supply 28, whereby a current to be supplied from the shim coil power supply 28 to the shim coil 22 is adjusted. This uniformalizes the static magnetic field formed inside the static field magnet 21.

Then, in step S12, when the operator instructs for acquisition of a frequency spectrum by the input unit 33, a sequence for frequency spectrum acquisition is provided from the imaging condition setting unit 48 to the sequence controller 31 through the sequence controller controlling unit 40.

Thereupon, the sequence controller 31 generates an X-axis gradient magnetic field Gx, a Y-axis gradient magnetic field Gy, a Z-axis gradient magnetic field Gz, and RF signals by driving the gradient power supply 27, the transmitter 29, and the receiver 30 based on the sequence for frequency spectrum acquisition. Then, MR signals generated by nuclear magnetic resonance of proton spins inside the object P are received by the RF coil 24, and provided to the frequency spectrum acquiring unit 49 through the receiver 30, the sequence controller 31 and the sequence controller controlling unit 40. The frequency spectrum acquiring unit 49 acquires a frequency spectrum from the MR signals, and the acquired frequency spectrum is provided to the resonant frequency detecting unit 50. Here, the frequency spectrum is provided to the display unit 34 and displayed thereon.

Next, the resonant frequency detecting unit 50 detects the resonant frequency of at least one substance from the frequency spectrum by a retrieving method designated by an operation of the input device 33 by the operator. For example, as the resonant frequency of water constituting the reference, a frequency corresponding to the maximum value in the frequency spectrum is automatically detected by the resonant frequency detecting unit 50. Alternatively, by an operation of the input device 33, the operator may associated the frequency corresponding to the maximum value in the frequency spectrum detected by the resonant frequency detecting unit 50 with the resonant frequency of water. The resonant frequency detecting unit 50 then provides the detected frequency to the frequency correcting unit 51, as the resonant frequency of water.

Here, if the frequency spectrum is of a shape such that the center frequency in the resonant frequency band of water takes the maximum value as shown in FIG. 4(a), the resonant frequency of water is provided to the frequency correcting unit 51. However, if the frequency spectrum is of a shape such that the center frequency in the resonant frequency band of silicone takes the maximum value as shown in FIG. 4(b), the resonant frequency of silicone is provided to the frequency correcting unit 51 in a state where it is erroneously recognized as the resonant frequency of water.

So in step S13, if the resonant frequency has been erroneously recognized, the resonant frequency of silicone is corrected to that of water by the frequency correcting unit 51. To this end, the frequency correcting unit 51 instructs the resonant frequency detecting unit 50 to detect frequencies and their positions corresponding to the peaks of the frequency spectrum. As a result, the frequencies and their positions corresponding to the peaks of the frequency spectrum, detected by the resonant frequency detecting unit 50 are provided to the frequency correcting unit 51, and displayed on the display unit 34.

When a manual misrecognition detection mode and manual correction mode to the resonant frequency are selected, the operator checks the display unit 34. When it is determined that the resonant frequency of silicone has been erroneously recognized as that of water, a frequency corresponding to the peak of the resonant frequency of water is designated by an operation of the input device 33. Alternatively, information that the chemical shift value of the resonant frequency of silicone with respect to that of water is −5 ppm, or that the resonant frequency of silicone has been erroneously acquired, may be inputted from the input device 33 to the frequency correcting unit 51, and a correction instruction may be provided to the frequency correcting unit 51.

On the other hand, when a manual misrecognition detection mode and automatic correction mode to the resonant frequency are selected, the frequency correcting unit 51 determines whether a frequency corresponding to the peak on the lower frequency side coincides with a frequency corresponding to the maximum value in the frequency spectrum. If the frequency corresponding to the peak on the lowest frequency side does not coincide with the frequency corresponding to the maximum value in the frequency spectrum, the frequency correcting unit 51 determines that the resonant frequency of silicone has been erroneously recognized as that of water. Furthermore, the frequency correcting unit 51 automatically shifts the resonant frequency of silicone by −5 ppm based on the chemical shift value of resonant frequency of the silicone with respect to water, thereby determining the correct resonant frequency of water.

Next, the frequency correcting unit 51 acquires the resonant frequency of each substance by making a zero-order correction of chemical shift data acquired from the chemical shift data storage unit 45 based on the acquired resonant frequency of water. As required, using frequency spectrum acquired by the frequency spectrum acquiring unit 49, the frequency correcting unit 51 corrects a first or higher order coefficients of chemical shift data acquired from the chemical shift data storage unit 45.

The frequency correcting unit 51 then provides the resonant frequencies of water and silicone, obtained by the corrections to the first frequency setting unit 53, second frequency setting unit 54, and magnetizing condition setting unit 55.

Next, in step S14, the first frequency setting unit 53 sets the center frequency of the 90° excitation pulse in the PASTA sequence to the resonant frequency of water, acquired from the frequency correcting unit 51. Also, the magnetizing condition setting unit 55 sets the frequency bandwidths BW90 and BW180, the $\tau$ lengths $\tau$90 and $\tau$180 of the 90° excitation pulse and 180° refocus pulse, and the gradient magnetic fields G90 and G180 for slice selection to be applied along with the 90° excitation pulse and 180° refocus pulse, respectively, so that the frequency bandwidth BW90 of the 90° excitation pulse does not overlap the resonant frequency bands of silicone and fat in the slice to be imaged, and simultaneously so that the frequency bandwidth BW180 of the 180° refocus pulse overlaps the resonant frequency bands of water, fat, and silicone in the slice to be imaged. The imaging condition setting unit 48 provides the PASTA sequence to the sequence controller controlling unit 40.

Then, in step S15, the PASTA sequence is provided from the sequence controller controlling unit 40 to the sequence controller 31, and a scan by the FSE+15_pasta is performed by control of the gradient power supply 27, transmitter 29, and receiver 30 by the sequence controller 31. As a consequence, data received in the RF coil 24 is disposed in the k-space formed in the k-space database 41 as k-space data through the receiver 30, the sequence controller 31, and the sequence controller controlling unit 40. Then, the image reconstructing unit 42 captures the k-space data from the k-space database 41 and applies image reconstructing processing to it, whereby a three-dimensional image data is reconstructed to thereby be written into the image database 43. Furthermore, the image processing unit 44 performs necessary image processing for the three-dimensional image data read from the image database 43, and causes the display unit 34 to display it.

Here, the image to be displayed on the display unit 34 is one that was obtained by selectively exciting the water area in order to prevent the fat area and silicone area from being excited by the 90° excitation pulse, and hence, this image is a water image with fat signals and silicone signals suppressed.

Next, in step S16, the second frequency setting unit 54 automatically sets the center frequency of the 90° excitation pulse in the PASTA sequence to the resonant frequency of silicone, acquired from the frequency correcting unit 51. That is, since the chemical shift of the resonant frequency of silicone is about −5 ppm with respect to the resonant frequency of water (0 ppm in chemical shift), the center frequency of the excitation pulse is automatically shifted by −5 ppm. Also, the magnetizing condition setting unit 55 sets the frequency bandwidths BW90 and BW180, the τ lengths τ90 and τ180 of the 90° excitation pulse and 180° refocus pulse, and the gradient magnetic fields G90 and G180 for slice selection to be applied along with the 90° excitation pulse and 180° refocus pulse, respectively, so that the frequency bandwidth BW90 of the 90° excitation pulse does not overlap the resonant frequency band of water in the slice to be imaged, and simultaneously so that the frequency bandwidth BW180 of the 180° refocus pulse overlaps the resonant frequency bands of water, fat, and silicone in the slice to be imaged. The imaging condition setting unit 48 then provides the PASTA sequence to the sequence controller controlling unit 40.

Then, in step S17, the PASTA sequence is provided from the sequence controller controlling unit 40 to the sequence controller 31, and a scan by the FSE+15_pastaSi without FatSat is performed. The image obtained by the scan is displayed on the display unit 34.

Here, the image to be displayed on the display unit 34 is one that was obtained by selectively exciting the fat area and silicone area in order to prevent the water area from being excited by the 90° excitation pulse, and hence, this image is an image with water signals suppressed and fat signals and silicone signals enhanced.

Then, instep S18, the fat saturation designating unit 56 adds a fat suppression pulse to the PASTA sequence used in the second-time scan. The imaging condition setting unit 48 provides this PASTA sequence to the sequence controller controlling unit 40. Consequently, the PASTA sequence is provided from the sequence controller controlling unit 40 to the sequence controller 31, and a scan by FSE+15_pastaSi with FatSat is performed. The image obtained by the scan is displayed on the display unit 34.

Here, the image to be displayed on the display unit 34 is one that was obtained by suppressing fat signals by the fat suppression pulse, and simultaneously by selectively exciting the silicone area in order to prevent the water area from being excited by the 90° excitation pulse, and hence, this image is an image with water signals and fat signals suppressed and silicone signals enhanced.

As a result, the operator makes reference to respective images obtained by performing the FSE+15_pasta and the FSE+15_pastaSi without FatSat, and thereby the operators can determine whether a breast implant is silicone or saline. Also, it is possible to detect an leakage of silicone by making a reference to respective images obtained by performing the FSE+15_pastaSi without FatSat and the FSE+15_pastaSi with FatSat.

In summary, the magnetic resonance imaging apparatus 20 as described above is one that is arranged to execute molecular imaging by adjusting the center frequency of excitation pulse and magnetizing conditions such as the time of τ length in accordance with the chemical shift value of a substance. The magnetic resonance imaging apparatus 20 is also one that is arranged to automatically change the center frequency of the excitation pulse when a plurality of substances is designated as targets of chemical imagings.

Therefore, according to the magnetic resonance imaging apparatus 20, if the chemical shift value of a particular component is known, automatically imaging of this component becomes feasible by inputting the chemical shift value of the component.

Moreover, according to the magnetic resonance imaging apparatus 20, the operator is capable of performing chemical shift imaging without the need for knowledge of chemical shift. Furthermore, according to the magnetic resonance imaging apparatus 20, when a plurality of substances is to be subjected to chemical shift imaging as in the case of an examination of a breast implant, there is no need to perform shimming, setting of center frequency and adjustment of magnetizing conditions for each scan, resulting in an improved convenience of the operator.

As an especially practical example, as long as silicone is designated, the center frequency of excitation pulse can be automatically set to that of silicone without the need for knowledge of chemical shift. Also, as long as water and silicone are designated, the resonant frequency of silicone can be excited by automatically shifting the center frequency of the excitation pulse by −5 ppm, after a scan for a water image.

Furthermore, according to the magnetic resonance imaging apparatus 20, the detection of the resonant frequency of a substance, detection of the erroneous recognition of a resonant frequency, and correction of the erroneously recognized resonant frequency can be performed in an automatic or manual manner. Hence, even if it is difficult for the operator to discern the difference in resonant frequency between substances, the resonant frequency of a predetermined substance can be automatically determined. Also, it is possible to reduce mistakes of the operator's erroneously setting the resonant frequency of an impertinent substance to the center frequency of excitation pulse. Particularly when the intensity of silicone signals is high, even if the silicone signals are erroneously recognized as water signals, they can be corrected to the correct water signals in an automatic or manual manner.

Moreover, it is also possible to perform chemical shift imaging by automatically detecting the center frequency of water from a frequency spectrum obtained by a pre-scan, and automatically setting the center frequency of excitation pulse to the detected center frequency of water. Such automatization of the detection of resonant frequency and of the setting of center frequency and/or magnetizing conditions enables an improvement in the convenience of an operator.

What is claimed is:

1. A magnetic resonance imaging apparatus comprising: a chemical shift data storage unit configured to store chemical shift data of a plurality of substances which are to be targets for chemical shift imaging; a first frequency adjusting unit configured to adjust a center frequency of a first excitation pulse to a resonant frequency of a designated first substance; a first imaging unit configured to acquire a first magnetic resonant signal from a region containing the first substance by performing a first chemical shift imaging scanning with the first excitation pulse and generate an image in which the first substance is enhanced by using the first magnetic resonant signal; a second frequency adjust unit configured to automatically adjust a center frequency of a second excitation pulse to a resonant frequency of a preliminarily designated second substance in accordance with chemical shift data about at least one of the first substance and the second substance stored in the chemical shift data storage unit; and a second imaging unit configured to acquire a second magnetic resonant signal from a region containing the second substance by performing a second chemical shift imaging scanning with the second excitation pulse and generate an image in which the second substance is enhanced by using the second magnetic resonant signal.

2. A magnetic resonance imaging apparatus according to claim 1, wherein the first imaging unit is configured to perform the first chemical shift imaging scanning by using one of a sequence in which a gradient magnetic field for slice selection showing a polarity opposite to that of another gradient magnetic field for slice selection applied with the first excitation pulse are applied with a refocus pulse following the first excitation pulse adjusted in at least one of a frequency band and a length of lobe so as to prevent overlapping with a resonant frequency band of the second substance, a sequence in which a period between component pulses generated by dividing an excitation pulse at a rate according to a binomial distribution is adjusted as a magnetizing condition in accordance with chemical shift data about the first substance so as to enhance the first magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the first substance so as to enhance the first magnetic resonance signal and the second imaging unit is configured to perform the second chemical shift imaging scanning by using one of a sequence in which a gradient magnetic field for slice selection showing a polarity opposite to that of another gradient magnetic field for slice selection applied with the second excitation pulse are applied with a refocus pulse following the second excitation pulse adjusted in at least one of a frequency band and a length of lobe so as to prevent overlapping with a resonant frequency band of the first substance, a sequence in which a period between component pulses generated by dividing an excitation pulse at a rate according to a binomial distribution is adjusted as a magnetizing condition in accordance with chemical shift data about the second substance so as to enhance the second magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the second substance so as to enhance the second magnetic resonance signal.

3. A magnetic resonance imaging apparatus according to claim 1, further comprising a substance designating unit configured to designate the first substance and the second substance by specifying one of a name of a substance to be an imaging target, a name of a sequence for imaging, a purpose of imaging and chemical shift data about the substance to be the imaging target.

4. A magnetic resonance imaging apparatus according to claim 1, further comprising: a frequency spectrum acquiring unit configured to acquire a frequency spectrum; a resonant frequency acquiring unit configured to acquire a resonant frequency of the first substance from the frequency spectrum; and a resonant frequency correcting unit configured to correct a resonant frequency of a substance different form the first substance to the resonant frequency of the first substance in accordance with the chemical shift data in case where the frequency spectrum acquiring unit erroneously acquires the resonant frequency of the substance different form the first substance as the resonant frequency of the first substance.

5. A magnetic resonance imaging apparatus according to claim 4, wherein the frequency spectrum acquiring unit is configured to acquire a frequency spectrum of water and the resonant frequency correcting unit is configured to correct a resonant frequency of silicone to a resonant frequency of the water in accordance with the chemical shift data in case where the frequency spectrum acquiring unit erroneously acquires the resonant frequency of the silicone as the resonant frequency of the water.

6. A magnetic resonance imaging apparatus comprising: a chemical shift data storage unit configured to store chemical shift data of a plurality of substances which are to be targets for chemical shift imaging; a first frequency adjusting unit configured to adjust a center frequency of a first excitation pulse to a resonant frequency of a first substance, the first substance being designated one of silicone and water; a first imaging unit configured to acquire a first magnetic resonant signal from a region containing the first substance by performing a first chemical shift imaging scanning with the first excitation pulse and generate an image in which the first substance is enhanced by using the first magnetic resonant signal; a second frequency adjust unit configured to automatically adjust a center frequency of a second excitation pulse to a resonant frequency of a second substance which is other of the silicone and the water in accordance with chemical shift data about the other stored in the chemical shift data storage unit; and a second imaging unit configured to acquire a second magnetic resonant signal from a region containing the second substance by performing a second chemical shift imaging scanning with the second excitation pulse and generate an image in which the second substance is enhanced by using the second magnetic resonant signal.

7. A magnetic resonance imaging apparatus according to claim 6, wherein the first imaging unit is configured to perform the first chemical shift imaging scanning by using one of a sequence in which a gradient magnetic field for slice selection showing a polarity opposite to that of another gradient magnetic field for slice selection applied with the first excitation pulse are applied with a refocus pulse following the first excitation pulse adjusted in at least one of a frequency band and a length of lobe so as to prevent overlapping with a resonant frequency band of the second substance, a sequence in which a period between component pulses generated by dividing an excitation pulse at a rate according to a binomial distribution is adjusted as a magnetizing condition in accordance with chemical shift data about the first substance so as to enhance the first magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the first substance so as to enhance the first magnetic resonance signal and the second imaging unit is configured to perform the second chemical shift imaging scanning by using one of a sequence in which a gradient magnetic field for slice selection showing a polarity opposite to that of another gradient magnetic field for slice selection applied with the second excitation pulse are applied with a refocus pulse following the second excitation pulse adjusted in at least one of a frequency band and a length of lobe so as to prevent overlapping with a resonant frequency band of the first substance, a sequence in which a period between component pulses generated by dividing an excitation pulse at a rate according to a binomial distribution is adjusted as a magnetizing condition in accordance with chemical shift data about the second substance so as to enhance the second magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the second substance so as to enhance the second magnetic resonance signal.

8. A magnetic resonance imaging apparatus according to claim 6, further comprising a substance designating unit configured to designate the first substance and the second substance by specifying one of a name of a substance to be an imaging target, a name of a sequence for imaging, a purpose of imaging and chemical shift data about the substance to be the imaging target.

9. A magnetic resonance imaging apparatus according to claim 6, further comprising:
a frequency spectrum acquiring unit configured to acquire a frequency spectrum; a resonant frequency acquiring unit configured to acquire a resonant frequency of the first substance from the frequency spectrum; and a resonant frequency correcting unit configured to correct a resonant frequency of a substance different form the first substance to the resonant frequency of the first substance in accordance with the chemical shift data in case where the frequency spectrum acquiring unit erroneously acquires the resonant frequency of the substance different form the first substance as the resonant frequency of the first substance.

10. A magnetic resonance imaging apparatus according to claim 9, wherein the frequency spectrum acquiring unit is configured to acquire a frequency spectrum of water and the resonant frequency correcting unit is configured to correct a resonant frequency of silicone to a resonant frequency of the water in accordance with the chemical shift data in case where the frequency spectrum acquiring unit erroneously acquires the resonant frequency of the silicone as the resonant frequency of the water.

11. A magnetic resonance imaging apparatus according to claim 6, further comprising a fat saturation imaging unit configured to acquire a magnetic resonance signal from a region containing the silicone with suppressing a signal from a region containing fat by performing chemical shift imaging scanning with applying a fat saturation pulse and generate an image in which the silicone is enhanced using the magnetic resonance signal.

12. A magnetic resonance imaging apparatus comprising: a substance designating unit configured to designate a substance which is to be a target for chemical shift imaging; a chemical shift data storage unit configured to store chemical shift data of substances which can be designated to the target; a frequency spectrum acquiring unit configured to acquire a frequency spectrum; a frequency adjusting unit configured to adjust a center frequency of an excitation pulse to a resonant frequency of silicone in accordance with chemical shift data of the silicone stored in the chemical shift data storage unit and the frequency spectrum in case where the silicone is designated by the substance designating unit; and an imaging unit configured to acquire a magnetic resonant signal from a region containing the silicone by performing chemical shift imaging scanning with the excitation pulse and generate an image in which the silicone is enhanced by using the magnetic resonant signal.

13. A magnetic resonance imaging apparatus according to claim 12, further comprising a fat saturation imaging unit configured to acquire a magnetic resonance signal from a region containing the silicone with suppressing a signal from a region containing fat by performing chemical shift imaging scanning with applying a fat saturation pulse and generate an image in which the silicone is enhanced using the magnetic resonance signal.

14. A magnetic resonance imaging apparatus according to claim 12, wherein the imaging unit is configured to performing the chemical shift imaging scanning by using one of a sequence in which a gradient magnetic field for slice selection showing a polarity opposite to that of another gradient magnetic field for slice selection applied with the excitation pulse are applied with a refocus pulse following the excitation pulse adjusted in at least one of a frequency band and a length of lobe so as to prevent overlapping with a resonant frequency band of water, a sequence in which a period between component pulses generated by dividing an excitation pulse at a rate according to a binomial distribution is adjusted as a magnetizing condition in accordance with chemical shift data about the silicone so as to enhance the magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the silicone so as to enhance the magnetic resonance signal.

15. A magnetic resonance imaging apparatus according to claim 12, wherein the substance designating unit configured to designate the substance which is to be the target by specifying one of a name of the substance to be an imaging target, a name of a sequence for imaging, a purpose of imaging and chemical shift data about the substance to be the imaging target.

16. A magnetic resonance imaging apparatus comprising: a substance designating unit configured to designate a substance which is to be a target for chemical shift imaging; a chemical shift data storage unit configured to store chemical shift data of substances which can be designated to the target; a frequency spectrum acquiring unit configured to acquire a frequency spectrum; a frequency adjusting unit configured to adjust a center frequency of an excitation pulse to a resonant frequency of the designated substance in accordance with chemical shift data about the designated substance stored in the chemical shift data storage unit and the frequency spectrum; and an imaging unit configured to perform chemical shift imaging scanning using a sequence of which a magnetizing condition is adjusted so as to enhance a magnetic resonance signal from the designated substance in accordance with chemical shift data about the designated substance and generate an image in which the designated substance is enhanced using the magnetic resonance signal acquired from a region containing the designated substance.

17. A magnetic resonance imaging apparatus according to claim 16, wherein the substance designating unit configured to designate the substance which is to be the target by specifying one of a name of the substance to be an imaging target, a name of a sequence for imaging, a purpose of imaging and chemical shift data about the substance to be the imaging target.

18. A magnetic resonance imaging apparatus according to claim 16, wherein the imaging unit is configured to perform the chemical shift imaging scanning by using a sequence in which a gradient magnetic field for slice selection showing a polarity opposite to that of another gradient magnetic field for slice selection applied with the excitation pulse are applied with a refocus pulse following the excitation pulse adjusted in at least one of a frequency band and a length of lobe so as to prevent overlapping with a resonant frequency band of a substance to be suppressed.

19. A magnetic resonance imaging apparatus according to claim 16, wherein the imaging unit is configured to perform the chemical shift imaging scanning by using a sequence in which a period between component pulses generated by dividing an excitation pulse at a rate according to a binomial distribution is adjusted as the magnetizing condition.

20. A magnetic resonance imaging apparatus according to claim 16, wherein the imaging unit is configured to perform the chemical shift imaging scanning by using a sequence in which a period between a refocus pulse and a .pi. pulse applied before the refocus pulse and a period between the refocus pulse and a -.pi. pulse applied after the refocus pulse are each adjusted as the magnetizing condition.

21. A magnetic resonance imaging apparatus comprising: a chemical shift data storage unit configured to store chemical shift data of at least one of a first substance and a second substance; a frequency spectrum acquiring unit configured to acquire a frequency spectrum; and a resonant frequency correcting unit configured to correct a resonant frequency of the second substance to a resonant frequency of the first substance in accordance with the chemical shift data in either of a case where the resonant frequency of the second substance is erroneously acquired as the resonant frequency of the first substance in accordance with the frequency spectrum and a case where the resonant frequency of the second substance is acquired to obtain the resonant frequency of the first substance in accordance with the frequency spectrum.

22. A magnetic resonance imaging apparatus according to claim 21, wherein the resonant frequency correcting unit is configured to correct a resonant frequency of silicone to a resonant frequency of water in either of a case where the resonant frequency of the silicone is erroneously acquired as the resonant frequency of the water and a case where the resonant frequency of the silicone is acquired to obtain the resonant frequency of the water.

23. A magnetic resonance imaging apparatus according to claim 21, wherein the resonant frequency correcting unit is configured to detect whether the resonant frequency of the second substance is erroneously acquired as the resonant frequency of the first substance in accordance with a position of a peak of the resonant frequency of the first substance on the frequency spectrum.

24. A magnetic resonance imaging method comprising steps of: adjusting a center frequency of a first excitation pulse to a resonant frequency of a designated first substance; acquiring a first magnetic resonant signal from a region containing the first substance by performing a first chemical shift imaging scanning with the first excitation pulse and generating an image in which the first substance is enhanced by using the first magnetic resonant signal; automatically adjusting a center frequency of a second excitation pulse to a resonant frequency of a preliminarily designated second substance in accordance with chemical shift data about at least one of the first substance and the second substance; and acquiring a second magnetic resonant signal from a region containing the second substance by performing a second chemical shift imaging scanning with the second excitation pulse and generating an image in which the second substance is enhanced by using the second magnetic resonant signal.

25. A magnetic resonance imaging method according to claim 24, wherein the first chemical shift imaging scanning is performed by using one of a sequence in which a gradient magnetic field for slice selection showing a polarity opposite to that of another gradient magnetic field for slice selection applied with the first excitation pulse are applied with a refocus pulse following the first excitation pulse adjusted in at least one of a frequency band and a length of lobe so as to prevent overlapping with a resonant frequency band of the second substance, a sequence in which a period between component pulses generated by dividing an excitation pulse at a rate according to a binomial distribution is adjusted as a magnetizing condition in accordance with chemical shift data about the first substance so as to enhance the first magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the first substance so as to enhance the first magnetic resonance signal and the second chemical shift imaging scanning is performed by using one of a sequence in which a gradient magnetic field for slice selection showing a polarity opposite to that of another gradient magnetic field for slice selection applied with the second excitation pulse are applied with a and a length of lobe so as to prevent overlapping with a resonant frequency band of the first substance, a sequence in which a period between component pulses generated by dividing an excitation pulse at a rate according to a binomial distribution is adjusted as a magnetizing condition in accordance with chemical shift data about the second substance so as to enhance the second magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the second substance so as to enhance the second magnetic resonance signal.

26. A magnetic resonance imaging method according to claim 24, further comprising a step of: designating the first substance and the second substance by specifying one of a name of a substance to be an imaging target, a name of a sequence for imaging, a purpose of imaging and chemical shift data about the substance to be the imaging target.

27. A magnetic resonance imaging method according to claim 24, further comprising a step of: acquiring a frequency spectrum; acquiring a resonant frequency of the first substance from the frequency spectrum; and correcting a resonant frequency of a substance different form the first substance to the resonant frequency of the first substance in accordance with the chemical shift data in case where the resonant frequency of the substance different form the first substance is erroneously acquired as the resonant frequency of the first substance.

28. A magnetic resonance imaging method according to claim 27, wherein a frequency spectrum of water is acquired and a resonant frequency of silicone is corrected to a resonant frequency of the water in accordance with the chemical shift data in case where the resonant frequency of the silicone is erroneously acquired as the resonant frequency of the water.

29. A magnetic resonance imaging method comprising steps of: adjusting a center frequency of a first excitation pulse to a resonant frequency of a first substance, the first substance being designated one of silicone and water; acquiring a first magnetic resonant signal from a region containing the first substance by performing a first chemical shift imaging scanning with the first excitation pulse and generating an image in which the first substance is enhanced by using the first magnetic resonant signal; automatically adjusting a center frequency of a second excitation pulse to a resonant frequency of a second substance which is other of the silicone and the water in accordance with chemical shift data about the other; and acquiring a second magnetic resonant signal from a region containing the second substance by performing a second chemical shift imaging scanning with the second excitation pulse and generating an image in which the second substance is enhanced by using the second magnetic resonant signal.

30. A magnetic resonance imaging method according to claim 29, wherein the first chemical shift imaging scanning is performed by using one of a sequence in which a gradient magnetic field for slice selection showing a polarity opposite to that of another gradient magnetic field for slice selection applied with the first excitation pulse are applied with a refocus pulse following the first excitation pulse adjusted in at least one of a frequency band and a length of lobe so as to prevent overlapping with a resonant frequency band of the second substance, a sequence in which a period between component pulses generated by dividing an excitation pulse at a rate according to a binomial distribution is adjusted as a magnetizing condition in accordance with chemical shift data about the first substance so as to enhance the first magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the first substance so as to enhance the first magnetic resonance signal and the second chemical shift imaging scanning is performed by using one of a sequence in which a gradient magnetic field for slice selection showing a polarity opposite to that of another gradient magnetic field for slice selection applied with the second excitation pulse are applied with a refocus pulse following the second excitation pulse adjusted in at least one of a frequency band and a length of lobe so as to prevent overlapping with a resonant frequency band of the first substance, a sequence in which a period between component pulses generated by dividing an excitation pulse at a rate according to a binomial distribution is adjusted as a magnetizing condition in accordance with chemical shift data about the second substance so as to enhance the second magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the second substance so as to enhance the second magnetic resonance signal.

31. A magnetic resonance imaging method according to claim 29, further comprising a step of: designating the first substance and the second substance by specifying one of a name of a substance to be an imaging target, a name of a sequence for imaging, a purpose of imaging and chemical shift data about the substance to be the imaging target.

32. A magnetic resonance imaging method according to claim 29, further comprising a step of: acquiring a frequency spectrum; acquiring a resonant frequency of the first substance from the frequency spectrum; and correcting a resonant frequency of a substance different form the first substance to the resonant frequency of the first substance in accordance with the chemical shift data in case where the resonant frequency of the substance different form the first substance is erroneously acquired as the resonant frequency of the first substance.

33. A magnetic resonance imaging method according to claim 32, wherein a frequency spectrum of water is acquired and a resonant frequency of silicone is corrected to a resonant frequency of the water in accordance with the chemical shift data in case where the resonant frequency of the silicone is erroneously acquired as the resonant frequency of the water.

34. A magnetic resonance imaging method according to claim 29, further comprising a step of acquiring a magnetic resonance signal from a region containing the silicone with suppressing a signal from a region containing fat by performing chemical shift imaging scanning with applying a fat saturation pulse and generating an image in which the silicone is enhanced using the magnetic resonance signal.

35. A magnetic resonance imaging method comprising steps of: designating a substance which is to be a target for chemical shift imaging; acquiring a frequency spectrum; adjusting a center frequency of an excitation pulse to a resonant frequency of silicone in accordance with chemical shift data of the silicone and the frequency spectrum in case where the silicone is designated as the substance which is to be the target; and acquiring a magnetic resonant signal from a region containing the silicone by performing chemical shift imaging scanning with the excitation pulse and generating an image in which the silicone is enhanced by using the magnetic resonant signal.

36. A magnetic resonance imaging method according to claim 35, further comprising a step of acquiring a magnetic resonance signal from a region containing the silicone with suppressing a signal from a region containing fat by performing chemical shift imaging scanning with applying a fat saturation pulse and generating an image in which the silicone is enhanced using the magnetic resonance signal.

37. A magnetic resonance imaging method according to claim 35, wherein the chemical shift imaging scanning is performed by using one of a sequence in which a gradient magnetic field for slice selection showing a polarity opposite to that of another gradient magnetic field for slice selection applied with the excitation pulse are applied with a refocus pulse following the excitation pulse adjusted in at least one of a frequency band and a length of lobe so as to prevent overlapping with a resonant frequency band of water, a sequence in which a period between component pulses generated by dividing an excitation pulse at a rate according to a binomial distribution is adjusted as a magnetizing condition in accordance with chemical shift data about the silicone so as to enhance the magnetic resonance signal and a sequence in which a period between a refocus pulse and a .pi. pulse applied before the refocus pulse and a period between the refocus pulse and a -.pi. pulse applied after the refocus pulse are each adjusted as a magnetizing condition in accordance with chemical shift data about the silicone so as to enhance the magnetic resonance signal.

38. A magnetic resonance imaging method according to claim 35, wherein the substance which is to be the target is designated by specifying one of a name of the substance to be an imaging target, a name of a sequence for imaging, a purpose of imaging and chemical shift data about the substance to be the imaging target.

39. A magnetic resonance imaging method comprising steps of: designating a substance which is to be a target for chemical shift imaging; acquiring a frequency spectrum; adjusting a center frequency of an excitation pulse to a resonant frequency of the designated substance in accordance with chemical shift data about the designated substance and the frequency spectrum; and performing chemical shift imaging scanning using a sequence of which a magnetizing condition is adjusted so as to enhance a magnetic resonance signal from the designated substance in accordance with chemical shift data about the designated substance and generating an image in which the designated substance is enhanced using the magnetic resonance signal acquired from a region containing the designated substance.

40. A magnetic resonance imaging method according to claim 39, wherein the substance which is to be the target is designated by specifying one of a name of the substance to be an imaging target, a name of a sequence for imaging, a purpose of imaging and chemical shift data about the substance to be the imaging target.

41. A magnetic resonance imaging method according to claim 39, wherein the chemical shift imaging scanning is performed by applying a gradient magnetic field for slice selection showing a polarity opposite to that of another gradient magnetic field for slice selection applied with the excitation pulse with a refocus pulse following the excitation pulse adjusted in at least one of a frequency band and a length of lobe so as to prevent overlapping with a resonant frequency band of a substance to be suppressed.

42. A magnetic resonance imaging method according to claim 39, wherein the chemical shift imaging scanning is performed by using a sequence in which a period between component pulses generated by dividing an excitation pulse at a rate according to a binomial distribution is adjusted as the magnetizing condition.

43. A magnetic resonance imaging method according to claim 39, wherein the chemical shift imaging scanning is performed by using a sequence in which a period between a refocus pulse and a .pi. pulse applied before the refocus pulse and a period between the refocus pulse and a -.pi. pulse applied after the refocus pulse are each adjusted as the magnetizing condition.

44. A magnetic resonance imaging method comprising:
acquiring a frequency spectrum of NMR responses from an object to be imaged, said responses emanating from different substances in said object;
correcting an NMR frequency of a second of said substances to a an NMR frequency of a first of said substances in accordance with stored chemical shift data for at least one of the first and second substances in either of (a) a case where the resonant frequency of the second substance is erroneously acquired as the resonant frequency of the first substance in accordance with the frequency spectrum and (b) a case where the resonant frequency of the second substance is acquired and used to obtain the resonant frequency of the first substance in accordance with the acquired frequency spectrum; and
outputting a corrected resonant frequency for subsequent use in NMR imaging of said object.

45. A magnetic resonance imaging method according to claim 44, wherein: a resonant frequency of silicone is corrected to a resonant frequency of water in either of (a) a case where the resonant frequency silicone is erroneously acquired as the resonant frequency of water and (b) a case where the resonant frequency of silicone is acquired and used to obtain the resonant frequency of water.

46. A magnetic resonance imaging method according to claim 44, further comprising:
detecting whether the resonant frequency of the second substance is erroneously acquired as the resonant frequency of the first substance by reference to a position of a peak resonant frequency on the frequency spectrum.

\* \* \* \* \*